US010716907B2

(12) United States Patent
Eicher et al.

(10) Patent No.: US 10,716,907 B2
(45) Date of Patent: Jul. 21, 2020

(54) NEBULIZER

(71) Applicant: Boehringer Ingelheim International GmbH, Ingelheim am Rhein (DE)

(72) Inventors: Joachim Eicher, Ingelheim am Rhein (DE); Josef Gatz, Moosbach (DE); Markus Mueller, Cham (DE); Herbert Wachtel, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 664 days.

(21) Appl. No.: 15/308,879

(22) PCT Filed: May 4, 2015

(86) PCT No.: PCT/EP2015/000900
§ 371 (c)(1),
(2) Date: Nov. 4, 2016

(87) PCT Pub. No.: WO2015/169428
PCT Pub. Date: Nov. 12, 2015

(65) Prior Publication Data
US 2017/0072149 A1    Mar. 16, 2017

(30) Foreign Application Priority Data

May 7, 2014    (EP) .................................... 14001603

(51) Int. Cl.
*A61M 15/00*    (2006.01)
*A61M 11/00*    (2006.01)
*B05B 11/00*    (2006.01)

(52) U.S. Cl.
CPC ........ *A61M 15/0081* (2014.02); *A61M 11/00* (2013.01); *A61M 11/007* (2014.02);
(Continued)

(58) Field of Classification Search
CPC .............. A61M 15/00; A61M 15/0081; A61M 15/0068; A61M 15/0065; A61M 15/007;
(Continued)

(56) References Cited

U.S. PATENT DOCUMENTS 5,349,945 A * 9/1994 Wass ................... A61M 15/009
128/200.14
5,833,088 A    11/1998 Kladders
(Continued)

FOREIGN PATENT DOCUMENTS

CA    2863504 A1    7/2013
CN    101141993 A    3/2008
(Continued)

OTHER PUBLICATIONS

International Preliminary Report on Patentability and Written Opinion for corresponding PCT application No. PCT/EP2015/000900, 19 pages, dated Nov. 17, 2016.

*Primary Examiner* — Bradley H Philips
*Assistant Examiner* — Savannah L Gabriel
(74) *Attorney, Agent, or Firm* — Matthew B. Dernier, Esq.

(57) ABSTRACT

A nebulizer is proposed which receives a container with a fluid and an indicator device. The indicator device stops further use of the container in a locked state when a predetermined number of uses has been reached or exceeded. In the locked state, a locking device locks the nebulizer against rotation in a partially tensioned state and, thus, against further use. After replacement of the container including the indicator device, the nebulizer can be used again.

31 Claims, 25 Drawing Sheets

(52) U.S. Cl.
CPC .... *A61M 15/0021* (2014.02); *A61M 15/0026* (2014.02); *A61M 15/0035* (2014.02); *A61M 15/0036* (2014.02); *A61M 15/0041* (2014.02); *A61M 15/0065* (2013.01); *A61M 15/0071* (2014.02); *A61M 15/0073* (2014.02); *B05B 11/0054* (2013.01); *B05B 11/308* (2013.01); A61M 2202/0468 (2013.01); A61M 2205/273 (2013.01); A61M 2205/583 (2013.01); A61M 2205/586 (2013.01); A61M 2207/10 (2013.01)

(58) Field of Classification Search
CPC .......... A61M 15/0071; A61M 15/0073; A61M 15/008; B05B 11/3059
USPC ........................................ 128/200.14, 200.17
See application file for complete search history.

(56) References Cited

U.S. PATENT DOCUMENTS

| | | | |
|---|---|---|---|
| 6,510,847 | B1 | 1/2003 | Helgesson |
| 7,823,584 | B2* | 11/2010 | Geser ................ A61M 15/0065 |
| | | | 128/200.17 |
| 8,132,565 | B2 | 3/2012 | Von Schuckmann |
| 8,474,447 | B2 | 7/2013 | Von Schuckmann |
| 8,656,910 | B2 | 2/2014 | Boeck |
| 8,950,393 | B2 | 2/2015 | Holakovsky |
| 2003/0178020 | A1 | 9/2003 | Scarrott |
| 2008/0029085 | A1* | 2/2008 | Lawrence ........... A61M 15/009 |
| | | | 128/200.14 |
| 2008/0173669 | A1 | 7/2008 | Pocock |
| 2009/0050149 | A1 | 2/2009 | Von Schuckmann |
| 2010/0229857 | A1 | 9/2010 | Von Schuckmann |
| 2011/0011393 | A1 | 1/2011 | Geser |
| 2011/0290242 | A1 | 12/2011 | Bach |
| 2012/0132199 | A1 | 5/2012 | Kiesewetter |
| 2013/0056888 | A1* | 3/2013 | Holakovsky ...... A61M 15/0065 |
| | | | 261/78.2 |
| 2013/0125880 | A1 | 5/2013 | Holakovsky |

FOREIGN PATENT DOCUMENTS

| | | |
|---|---|---|
| CN | 102665806 A | 9/2012 |
| CN | 103272730 A | 9/2013 |
| CN | 103582505 A | 2/2014 |
| EP | 0684047 A2 | 11/1995 |
| EP | 2614848 A1 | 7/2013 |
| GB | 2398253 A1 | 8/2004 |
| JP | 2003524280 A | 2/2003 |
| JP | 2005305370 A | 11/2005 |
| JP | 2009505703 A | 2/2009 |
| NZ | 20030538925 A | 3/2007 |
| WO | 9606011 A2 | 2/1996 |
| WO | 0103851 | 1/2001 |
| WO | 2007104694 A1 | 9/2007 |
| WO | 2009037085 A1 | 3/2009 |
| WO | 2009115200 A1 | 9/2009 |
| WO | 2011064164 A1 | 6/2011 |
| WO | 2012160047 A2 | 11/2012 |
| WO | 2012160052 A1 | 11/2012 |
| WO | 2012162305 A1 | 11/2012 |
| WO | 2015169428 A2 | 11/2015 |

* cited by examiner

NEBULIZER

BACKGROUND

The present invention relates to a nebulizer.

WO 2012/162305 A1 discloses a nebulizer. A container can be inserted into a housing of the nebulizer. The housing is closed by a lower housing part By rotating the housing part the drive spring can be put under tension and fluid can be sucked into a compression chamber of the pressure generator. Simultaneously, the container is moved into the lower housing part in a stroke movement within the nebulizer and when tensioned for the first time the container may be pierced through its base by a piercing element in the lower housing part to allow venting of the container. After manually pressing a button, the drive spring is released and moves the delivery tube into the pressure chamber so that the fluid is put under pressure by the drive spring and is delivered or atomized through a nozzle into a mouthpiece as an aerosol, without the use of propellant gas. Thus, the container is moving axially forth and back during conveying of the fluid to be nebulized, and during pressure generation and nebulization.

The container may be connected inseparably with the housing part by a securing device forming a transportation lock for holding the container unmovable in a delivery state.

The nebulizer comprises an indicator device for counting and/or indicating a number of uses performed or still possible. The indicator device blocks further use in a locked state when a predetermined number of uses has been reached or exceeded with the current container. Then, the container can be replaced together with a housing part and the nebulizer can be used further with the new container.

U.S. Pat. No. 7,823,584 B2 discloses a similar nebulizer, wherein a counter device can be integrated into a housing part that is exchangeable or replaceable together with the container, which is inseparable from the housing part. The nebulizer comprises a locking device for blocking the lower housing part and an inner housing part against further rotation in a second locked state after a predetermined number of containers has been used to finally lock the nebulizer against any further use. This locking device comprises a spring as locking element which radially engages into an upper housing part of the nebulizer to block any further rotation when the nebulizer has been tensioned for the last time. The rotational locking cannot be unlocked again.

WO 2007/104694 A1 discloses an inhaler for powdery substances with an indicator device which may comprise a worm gear for driving an indicator element.

SUMMARY

Object of the present invention is to provide a nebulizer allowing easy and/or secure operation and handling and/or a compact and/or reliable construction, preferably while allowing replacement of the container without replacement of any housing part of the nebulizer.

The above object is achieved by a nebulizer as disclosed in the preferred embodiments.

The present invention relates to a nebulizer for nebulizing a fluid, preferably liquid medicament, from a preferably replaceable container containing the fluid. Preferably, an indicator device is provided for counting and/or indicating the number of uses already performed or still possible with the container.

In particular, the indicator device controls or causes a locking device to lock the nebulizer against further use in a locked state when a predetermined number of uses has been reached or exceeded with the respective container. Preferably, the nebulizer comprises a housing part which can be detached from the nebulizer or opened for replacing the container.

In particular, the locking device or a locking element thereof is adapted to block any (further) rotation of the nebulizer, in particular of a lower or detachable and/or inner housing part relative to an upper housing part of the nebulizer. Thus, the nebulizer cannot be tensioned or prepared for the next use, so that e.g. any pumping or dispensing of fluid is prevented, when the rotation is blocked in the locked state. In particular, (complete) tensioning is necessary for preparing the nebulizer for next use, i.e. next nebulization of fluid.

According to one aspect of the present invention, the locking device or locking element is adapted to block the rotation preferably before a complete tensioned state or position of the nebulizer is reached and/or in an intermediate position or partially tensioned state, most preferably in the second half of the total rotation angle necessary for (completely) tensioning the nebulizer. This allows easy and/or secure operation and handling. In particular, any further dispensing of fluid can be directly prevented when the locked state is entered as the nebulizer or its drive spring cannot be (completely) tensioned.

According to a further aspect of the present invention, the container is replaceable preferably only in an at least partially tensioned state of the nebulizer such that complete closing of the nebulizer or its housing is not possible when the indicator device is in the locked state. This allows easy and/or secure operation and handling. In particular, a user can easily realize that the indicator device preferably together with the container has to be changed and cannot be reused when the nebulizer cannot be closed.

According to another preferred aspect of the present invention, a locking element of the locking device axially engages by form-fit and/or with multiple, preferably rib-like engagement portions into respective pockets or vice versa in a locking position to block the rotation. This allows secure operation and/or simple construction, wherein a very quick locking can be achieved even if the nebulizer or its housing part is rotated with high speed. Further, a simple construction or easy operation for unlocking or release are possible.

According to a further aspect of the present invention, the locking device comprises preferably an axially moveable locking member interacting with the locking element via an inclined surface for radially moving the locking element preferably outwards into the locking position. Alternatively or additionally, the locking element is formed by or comprises a sliding block. The locking element or sliding block is preferably (only) radially moveable. This allows secure operation and/or simple construction, wherein a very quick locking can be achieved even if the nebulizer or its housing part is rotated with high speed. Further, a simple construction or easy operation for unlocking or release are possible.

According to another aspect of the present invention, the locking device and/or locked state can preferably be reset to release or unlock the rotation locking. This allows replacement of the container and indicator device, wherein the nebulizer and its housing part can be reused, while a very secure locking and, thus, secure operation can be realized in the locked state.

Preferably the container cannot be used anymore in the locked state when the indicator device has detected that a predetermined number of uses has been reached or exceeded, in particular with the respective container.

The indicator device may either directly or indirectly lock or initiate or trigger locking of the nebulizer and/or container against further use. In particular, the indicator device may directly actuate the locking device or indirectly initiate actuation of the locking device. Preferably, the indirect actuation is realized by means or via at least partial opening of the nebulizer or its housing or housing part in order to lock the nebulizer against further use with the current container.

Preferably, the nebulizer is blocked (automatically) against further use or tensioning if the nebulizer housing or housing part is at least partially open or opened or if, with other words, when the nebulizer or its housing is not (completely) closed.

It is also possible that the nebulizer is not immediately blocked against further use when the indicator device enters the locked state. Instead, the indicator device may initiate or cause or trigger in its locked state that the locking device is going to block the nebulizer against further use, e.g. during the next actuation or tensioning or the like. Thus, the locking device may enter its locking state later, e.g. after at least partial opening of the nebulizer and/or at least partial tensioning of the nebulizer or rotation of the housing part or inner part of the nebulizer or the like.

Therefore, the blocking of the nebulizer can be initiated or caused by the indicator device not only indirectly, but alternatively or additionally also later during further handling, operation, actuation or the like. In the latter case, the indicator device blocks or initiates or causes blocking of the nebulizer and/or container against further use also preferably in the sense of the present invention.

Preferably, the locking of the nebulizer against further use can be overcome by replacing the container, in particular including the indicator device, against one not yet used.

Preferably, the indicator device is inseparably connected with the container or with a container housing of the container, but separable from the nebulizer or its housing and from the housing part, so that the indicator device is replaceable together with the container. This allows reuse of the nebulizer and the housing part with another container including another indicator device. Thus the overall size of the components to be exchanged is kept small, so that the replacement packages are size reduced, so that transport of a large number of packages is facilitated.

Preferably, the indicator device is fixedly arranged at a bottom of the container and/or opposite to an outlet of the container. This allows a very compact construction. Further, the indicator device does not interfere with the fluidic connection of the container to the nebulizer or vice versa.

The above aspects of the present invention and the further aspects described below can be realized independently from each other, and in any combination.

Further advantages, features, characteristics and aspects of the present invention will become apparent from the claims and the following description of preferred embodiments with reference to the drawings. It shows:

DETAILED DESCRIPTION

Figure 1:
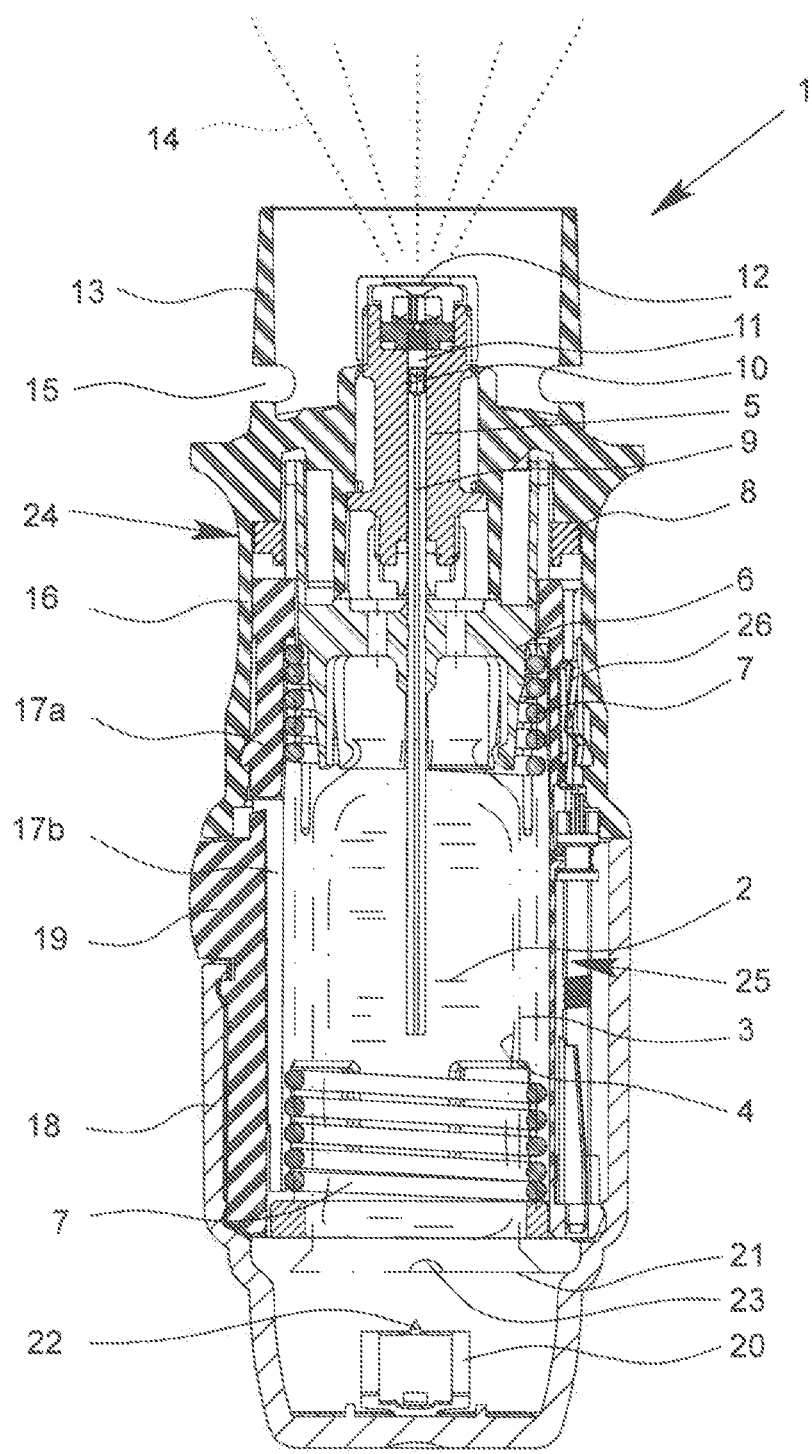
FIG. 1 a schematic section of a known nebulizer in a non-tensioned state.

In the Figures, the same reference numerals are used for identical or similar parts, resulting preferably in corresponding or comparable properties and advantages, even if the associated description is not repeated.

Figure 2:
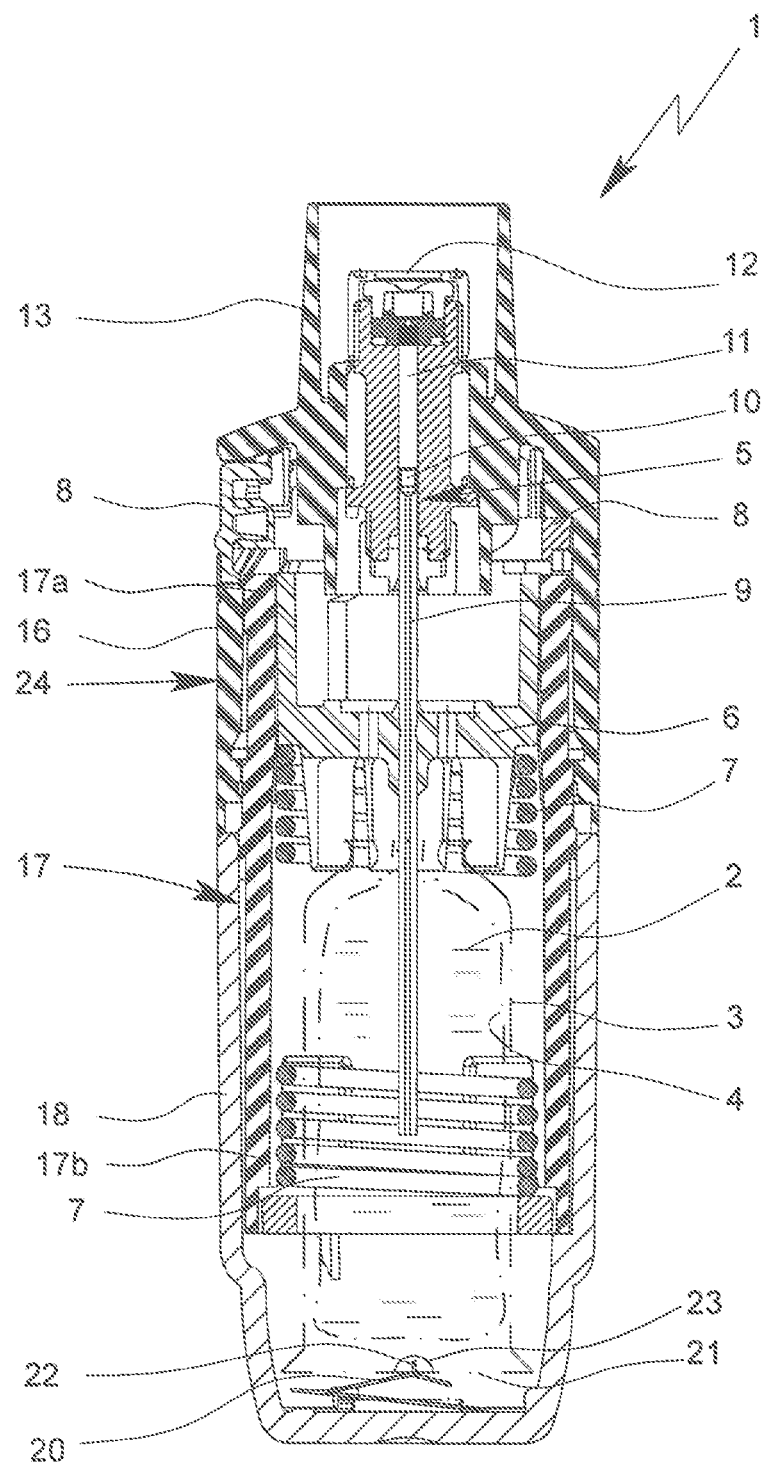
FIG. 2 a schematic section, rotated 90° compared with FIG. 1, of the known nebulizer in a tensioned state.

FIGS. 1 and 2 show a known nebulizer 1 for atomizing a fluid 2, particularly a highly effective pharmaceutical composition, medicament or the like, diagrammatically shown in a non-tensioned state (FIG. 1) and in a tensioned state (FIG. 2). The nebulizer 1 is constructed in particular as a portable inhaler and preferably operates only mechanical and/or without propellant gas.

When the fluid 2, preferably a liquid, more particularly a pharmaceutical composition, is nebulized, an aerosol 14 (FIG. 1) is formed or dispensed, which can be breathed in or inhaled by a user. Usually the inhaling is done at least once a day, more particularly several times a day, preferably at set intervals, depending on the complaint or illness from which a patient is suffering.

The nebulizer 1 is provided with or comprises an insertable or replaceable container 3 containing the fluid 2. The container 3 thus forms a reservoir for the fluid 2, which is to be nebulized. Preferably, the container 3 contains multiple doses of fluid 2 or active substance in particular sufficient to provide up to 200 dosage units or doses, for example, i.e. to allow up to 200 sprays or applications. A typical container 3, as disclosed in WO 96/06011 A1, holds e.g. a volume of about 2 to 20 ml.

Further, the number of doses contained in the container 3 and/or the total volume of the fluid 2 contained in the container 3 can vary depending on the fluid 2 or respective medicament and/or depending on the container 3 and/or depending on the necessary medication or the like.

Preferably, the container 3 can be replaced or exchanged, wherein the total number of uses of the nebulizer 1 and thus the number of containers 3, which can be used with the same nebulizer 1, is preferably restricted, e.g. to a total number of four or five containers 3. WO 2012/162305 A1 discloses additionally such a restriction to the total numbers of containers 3 which can be used with the same nebulizer 1.

The container 3 is preferably substantially cylindrical or cartridge-shaped and once the nebulizer 1 has been opened the container 3 can be inserted therein preferably from below and changed if desired. It is preferably of rigid construction, the fluid 2 in particular being held in a collapsible bag 4 in the container 3. In particular, the container 3 comprises a venting opening or hole 23 which is opened before or during first use.

The nebulizer 1 comprises a delivery mechanism, preferably a pressure generator 5, for conveying and nebulizing the fluid 2, particularly in a preset and optionally in an adjustable dosage amount.

The nebulizer 1 or pressure generator 5 comprises preferably a holder 6 for releasably holding the container 3, a drive spring 7 associated to the holder 6, only partly shown, and/or a blocking element 8 preferably in form of or with a button for preferably manual actuation or depressing. The blocking element 8 can catch and block the holder 6 and can be manually operated to release the holder 6 allowing drive spring 7 to expand.

The nebulizer 1 or pressure generator 5 comprises preferably a conveying element, such as a conveying tube 9, a non-return valve 10, a pressure chamber 11 and/or an nozzle 12 for nebulizing the fluid 2 into a mouthpiece 13.

The completely inserted container 3 is fixed or held in the nebulizer 1 via the holder 6 such that the conveying element fluidically connects the container 3 to the nebulizer 1 or pressure generator 5. Preferably, the conveying tube 9 penetrates into the container 3.

The nebulizer 1 or holder 6 is preferably constructed so that the container 3 can be exchanged.

When the drive spring 7 is axially tensioned in the tensioning process, the holder 6 with the container 3 and the conveying tube 9 are moved downwards in the drawings and fluid 2 is sucked out of the container 3 into the pressure chamber 11 of the pressure generator 5 through the non-return valve 10. In this state, the holder 6 is caught by the blocking element 8 so that the drive spring 7 is kept compressed. Then, the nebulizer 1 is in the tensioned state.

During the subsequent relaxation in the nebulization process after actuation or pressing of the blocking element 8 the fluid 2 in the pressure chamber 11 is put under pressure as the conveying tube 9 with its now closed non-return valve 10 is moved back in the pressure chamber 11, here in the drawings upwards, by the relaxation or force of the drive spring 7 and now acts as a pressing ram or piston. This pressure forces the fluid 2 through the nozzle 12, whereupon it is nebulized into the aerosol 14, as shown in FIG. 1, and, thus, dispensed.

Generally, the nebulizer 1 operates with a spring pressure of 5 to 200 MPa, preferably 10 to 100 MPa on the fluid 2, and/or with a volume of fluid 2 delivered per stroke of 10 to 50 preferably 10 to 20 most preferably about 15 The fluid 2 is converted into or nebulized as aerosol 14, the droplets of which have an aerodynamic diameter of up to 20 μm, preferably 3 to 10 μm. Preferably, the generated jet spray has an angle of 20° to 160°, preferably 80° to 100°. These values also apply to the nebulizer 1 according to the teaching of the present invention as particularly preferred values.

A user or patient (not shown) can inhale the aerosol 14, preferably while an air supply can be sucked into the mouthpiece 13 through at least one optional air supply opening 15.

The nebulizer 1 comprises preferably a housing 24 and/or (upper) housing part 16 and optionally a biasing or inner part 17 preferably which is rotatable relative thereto (FIG. 2) and/or has an upper part 17a and a lower part 17b (FIG. 1).

The nebulizer 1 or housing 24 comprises preferably a (lower) housing part 18. This part 18 is in particular manually operable, and/or releasable fixed, particularly fitted or held onto the inner part 17, preferably by means of a retaining element 19.

Preferably, the housing parts 16 and 18 and/or other parts form the housing 24 of the nebulizer 1.

In order to insert and/or replace the container 3, preferably the housing 24 can be opened and/or the housing part 18 can be detached from the nebulizer 1, inner part 17 or housing 24.

Generally and preferably, the container 3 can be inserted before the housing 24 is closed and/or before the housing part 18 is connected to the housing 24. The container 3 may be inserted, opened and/or fluidically connected to the delivery mechanism automatically or simultaneously when (completely) connecting the housing part 18 to the housing 24/nebulizer 1 and/or when (completely) closing the housing 24/nebulizer 1. Preferably, the container 3 is open or fluidically connected when tensioning the nebulizer 1 for the first time with the current container 3.

Preferably, the nebulizer 1 or drive spring 7 can be manually activated or tensioned or loaded, in particular by actuation of an actuation member, here preferably by rotating housing part 18 or any other component.

The actuation member, preferably the housing part 18, can be actuated, here rotated relative to the upper housing part 16, carrying with it or driving the inner part 17. The inner part 17 acts on a gear or transmission to transform the rotation in an axial movement. As a result the drive spring 7 is tensioned in the axial direction by means of the gear or transmission (not shown) formed between the inner part 17, in particular its upper part 17a, and the holder 6 and acting on the holder 6. During tensioning the container 3 is moved axially downwards until the container 3 assumes an end position as shown in FIG. 2. In this activated or tensioned state the drive spring 7 is under tension and can be caught or held by the blocking element 8. During the nebulizing process the container 3 is moved back into its original position (non-tensioned position or state shown in FIG. 1) by (the force of) the drive spring 7. Thus the container 3 executes a lifting or stroke movement during the tensioning process and during the nebulizing process.

The housing part 18 preferably forms a cap-like lower housing part and/or fits around or over a lower free end portion of the container 3. As the drive spring 7 is tensioned the container 3 moves with its end portion (further) into the housing part 18 or towards the end face thereof, while an aeration means, such as an axially acting spring 20 arranged in the housing part 18, comes in contact with base 21 of the container 3 and pierces the container 3 or a base seal or foil 50 thereon with a piercing element 22 when the container 3 makes contact with it for the first time, to allow air in or aeration, preferably by opening or piercing venting hole 23. The venting hole 23 allows for pressure compensation inside the container 3 when fluid 2 is drawn from the container 3 during the actuation of the nebulizer 1.

The nebulizer 1 comprises preferably an indicator device 25, which counts in particular actuations of the nebulizer 1, preferably by detecting its tensioning or the rotation of the inner part 17 relative to the upper part 16 or housing 24. Preferably, the counter device 25 or an associated locking device 26 locks the nebulizer 1 against (further) actuation or use, e.g. blocks further rotation of the housing part 18/inner part 17 and, thus, tensioning of the nebulizer 1 or its drive spring 7 and/or blocks actuation of the blocking element 8, in a locked state when a certain number of actuations or operations or discharged doses has been reached or exceeded.

In particular, the locking device 26 is controlled or controllable by the indicator device 25.

In the following and with reference to the further figures, a preferred embodiment of the nebulizer 1, container 3, indicator device 25 and/or locking device 26 is described and shown according to the invention, wherein primarily important aspects and differences will be described and the previous aspects, features and explanations apply preferably additionally or correspondingly even without repetition.

Figure 3:
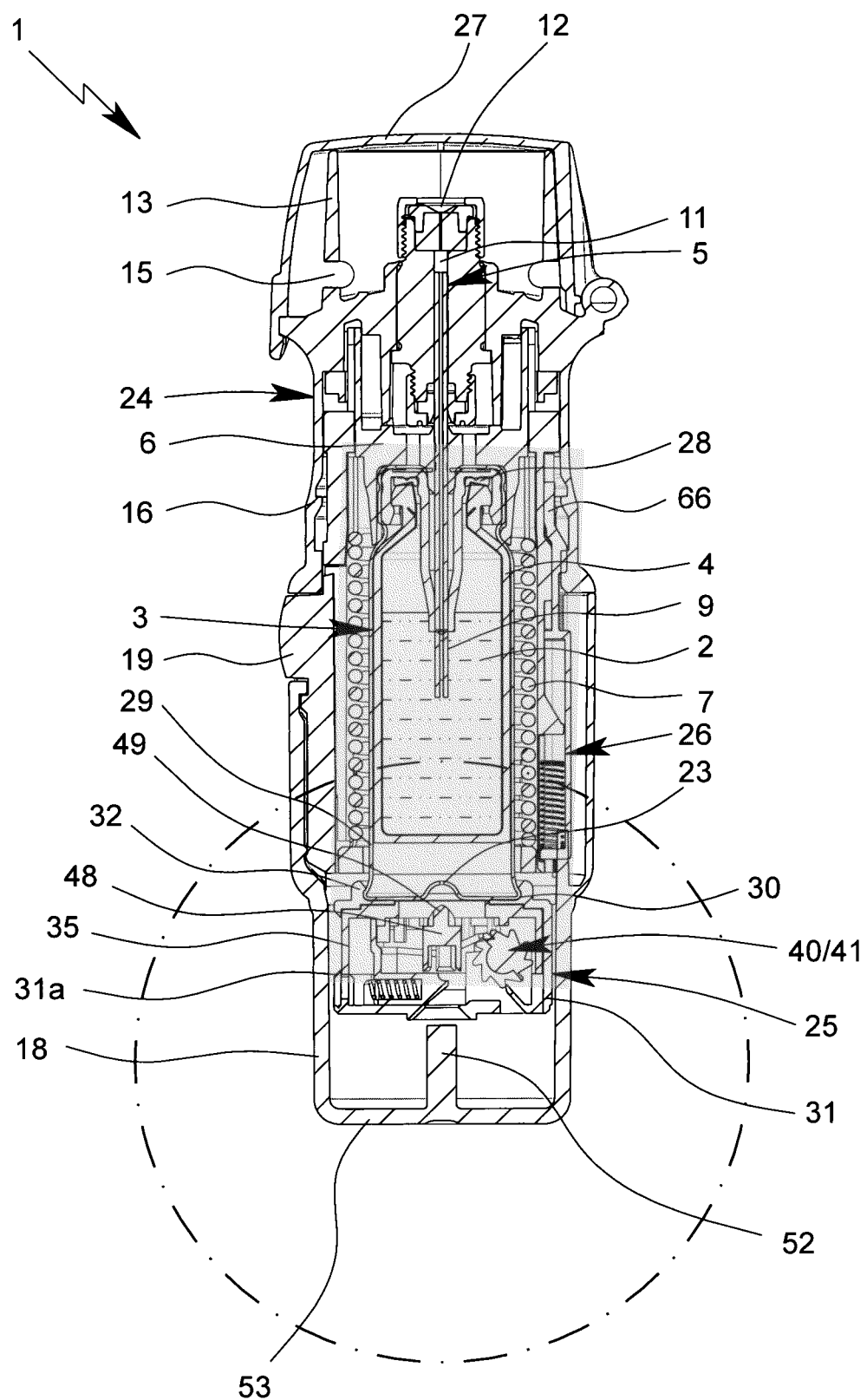
FIG. 3 a schematic section of a nebulizer with an inserted container in a non-tensioned state according to a preferred embodiment of the present invention.

FIG. 3 shows the nebulizer 1 with the container 3 and indicator device 25 according the present invention in a schematic section (longitudinal section) in the non-tensioned state with completely closed nebulizer housing 24 and, thus, closed housing part 18, wherein the container 3 including the proposed indicator device 25 are inserted into or received within the nebulizer 1 and/or housing 24.

Figure 4:
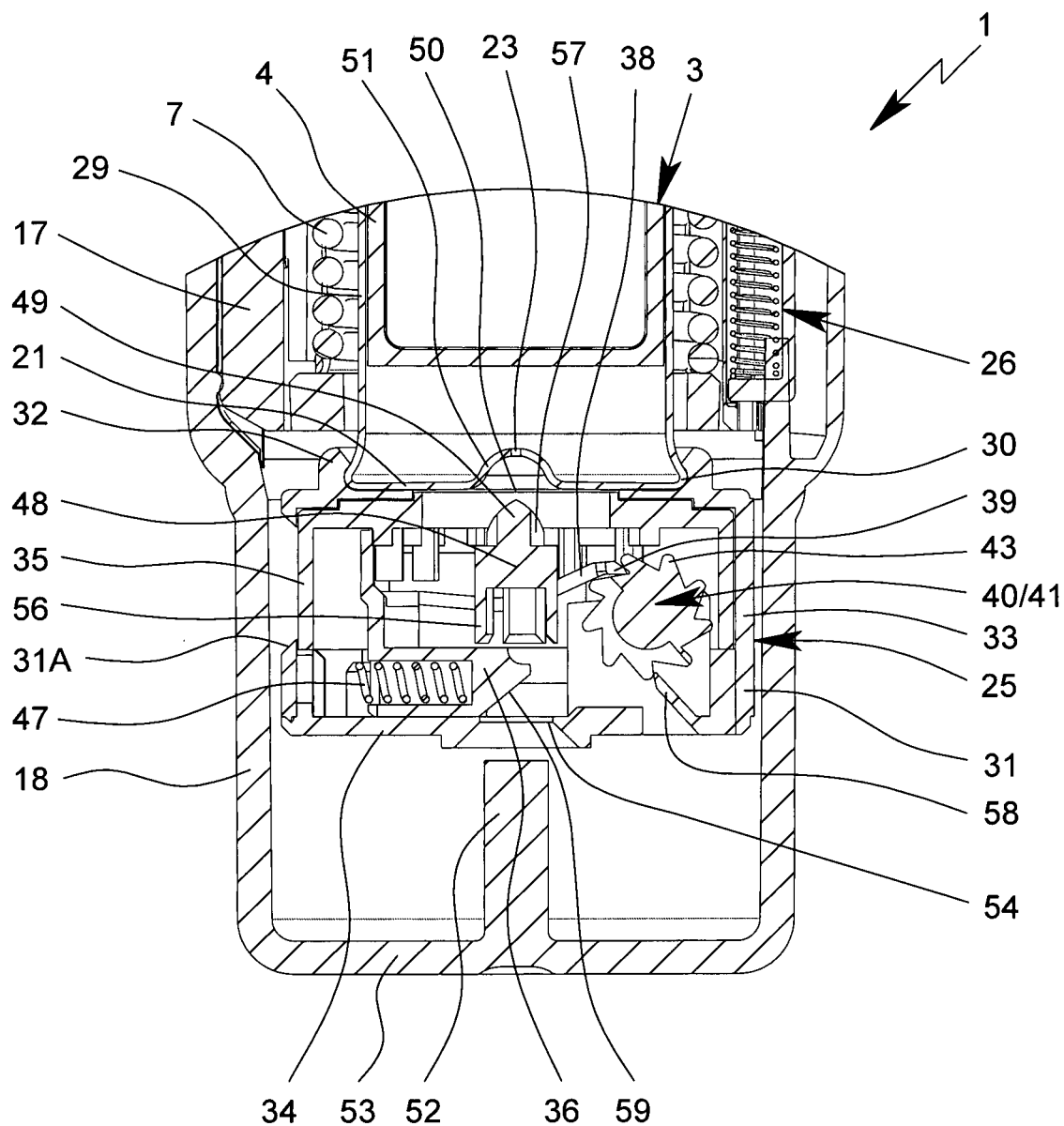
FIG. 4 a partial enlargement of the encircled part of FIG. 3.
Figure 5:
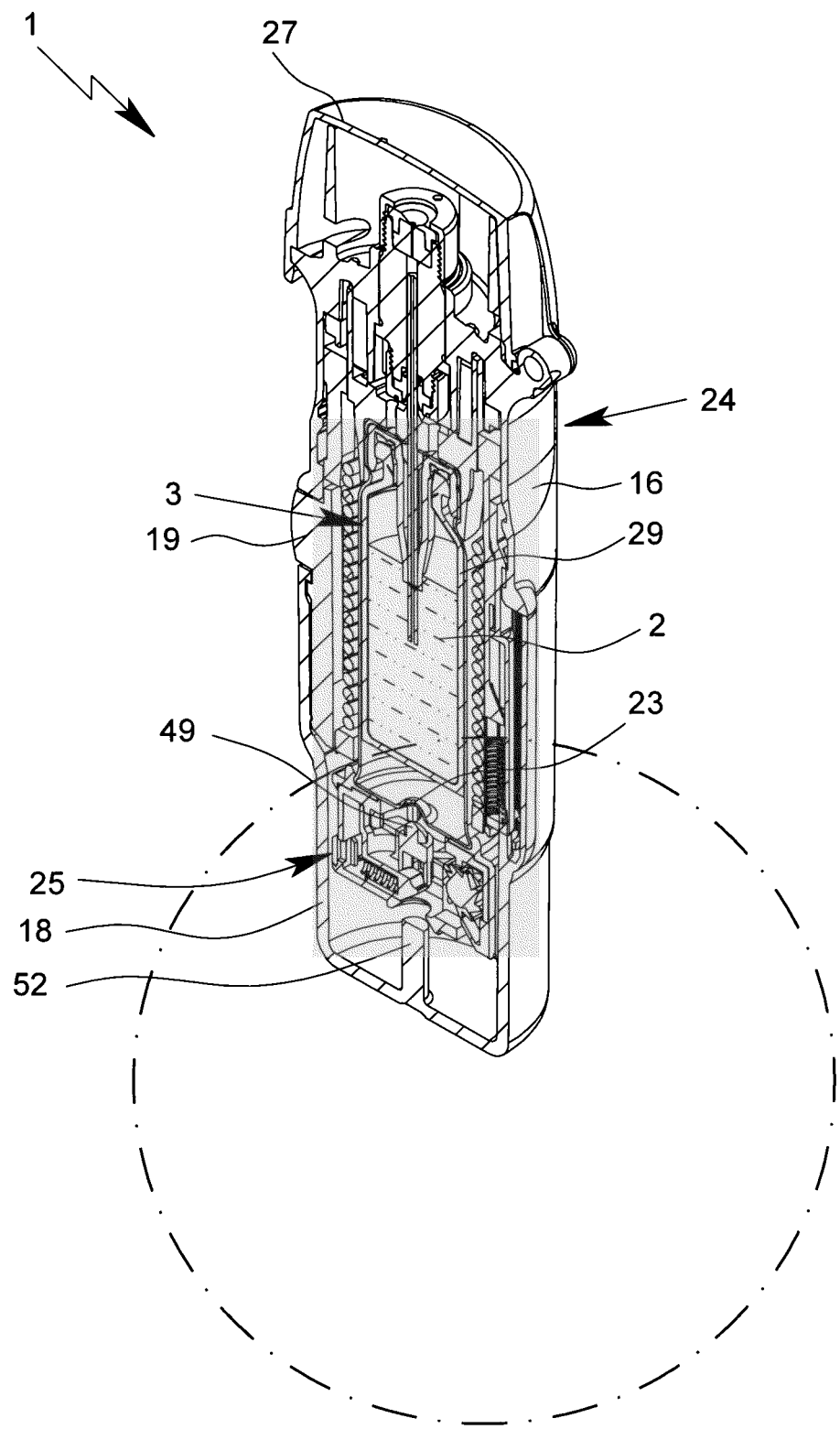
FIG. 5 a perspective view of the section of the nebulizer according to FIG. 3.
Figure 6:
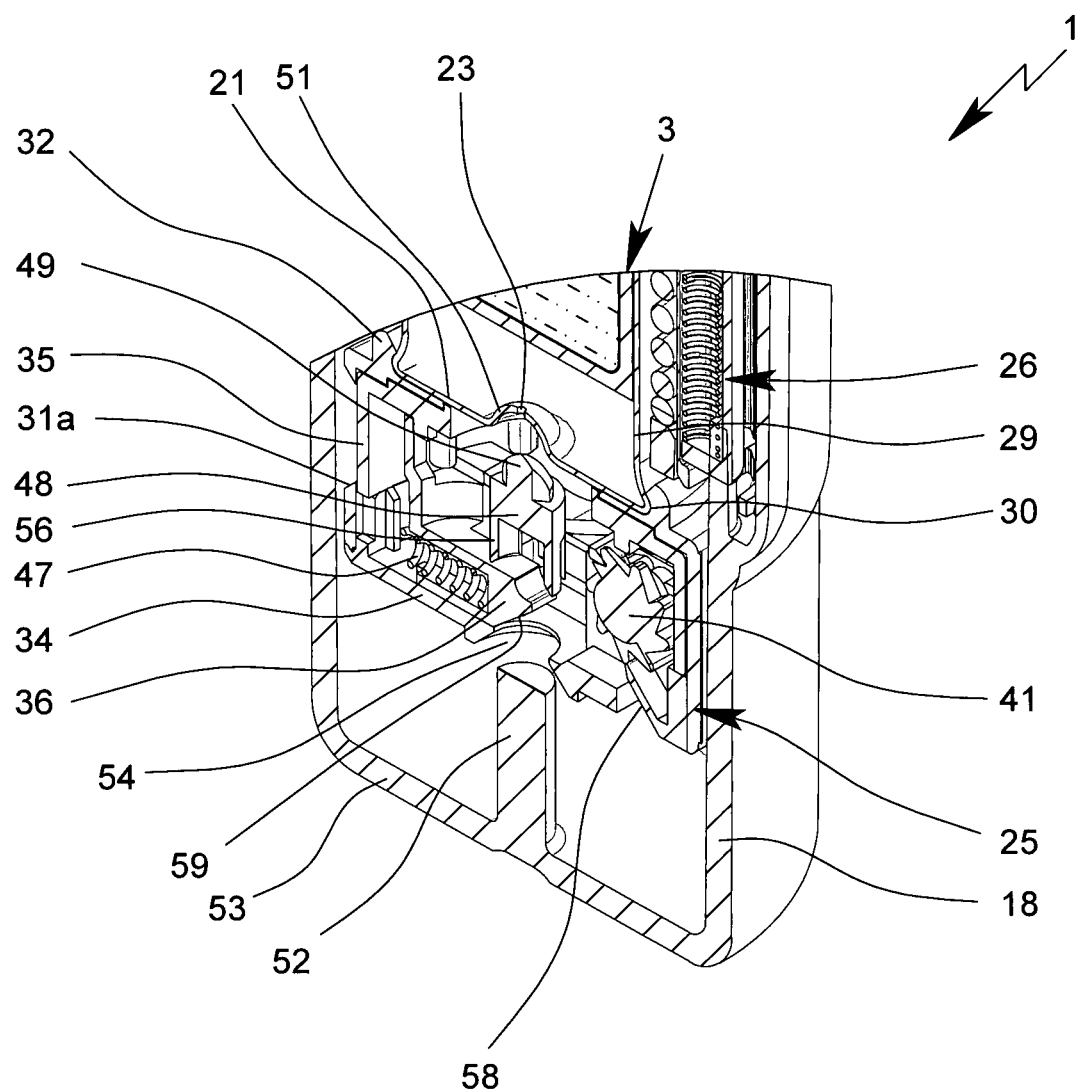
FIG. 6 an enlargement of the encircled part of FIG. 5.

FIG. 4 shows an enlarged partial section of the encircled part of FIG. 3. FIG. 5 shows a perspective view of the section of the nebulizer 1 of FIG. 3. FIG. 6 shows a partial enlargement of the encircled part of FIG. 5.

The nebulizer 1 has preferably a longitudinal form or axis which corresponds to the axial direction and/or to the main dispensing direction and/or to stroke movement of the container 3 during tensioning and dispensing.

In the shown non-tensioned state, the nebulizer 1 or its mouthpiece 13 is preferably closed by a mouthpiece cover 27. The mouthpiece cover 27 is preferably pivotable to allow opening of the mouthpiece 13 for using the nebulizer 1.

Preferably, the indicator device 25 is directly and/or unreleasably secured or fixed to or connected with the container 3. In particular, the indicator device 25 is associated to a respective container 3. If the container 3 of the nebulizer 1 is replaced, the indicator device 25 is necessarily or positively replaced as well.

Preferably, the indicator device 25 is fixedly arranged at the bottom of, or container base 21 of, the container 3 and/or opposite to an outlet or head 28 of the container 3.

In the present embodiment, the indicator device 25 is preferably directly connected to or abuts at an outer case or preferably rigid housing 29 of the container 3.

Preferably, the indicator device 25 and the container 3 are connected by form-fit and/or snap-fit.

In particular, the indicator device 25 circumvents and/or grips over a (lower or bottom) edge 30 and/or any other protrusion or the like of the container 3. In the present embodiment, the edge 30 is a little bit wider in diameter so that it protrudes radially over the essentially cylindrical outer form of the side wall of the container 3/container housing 29.

The diameter of the indicator device 25 is preferably at least essentially equal to or slightly greater than the diameter of the container 3 or its edge 30.

The edge 30 is preferably formed between the side wall and the bottom or base 21 of the container 3 or container housing 29. Preferably, the edge 30 is formed by flanging, bordering, bending or crimping or by any other suitable material-deforming process.

The indicator device 25 comprises a housing 31 and/or preferably has an at least essentially cylindrical form.

The indicator device 25 or its housing 31 is preferably attached to the container 3 or its base 21 or housing 29 with an at least essentially flat and/or axial side.

The indicator device 25 or its housing 31 comprises preferably a holding or gripping section 32 for connecting the indicator device 25 with the container 3. Preferably, the gripping section 32 circumvents the edge 30 and/or grips around or over the edge 30.

In the present embodiments, the gripping section 32 is preferably annular and/or grips over the edge 31 at positions distributed over the circumference of the edge 30 or container 3.

Preferably, the indicator device 25 and the container 3 are connected with each other by a snap-fit or click connection. Preferably, the container 3 and the indicator device 25 are connected with each other by axially snapping one part on the other.

Preferably, the gripping section 32 is sufficiently elastic in radial direction so that the container 3 can be entered axially with its edge 30. In the present embodiment, the gripping section 32 preferably comprises a respectively inclined insertion face to facilitate insertion of edge 30 into the annular gripping section 32 or between circumferentially distributed gripping sections 32.

It has to be noted that other constructional solutions are possible for connecting the container 3 or its housing 29 with the indicator device 25 or its housing 31 or vice versa. In particular, the two parts can be connected with each other additionally or alternatively by welding, brazing, gluing, screwing, clamping, hot-pressing, or the like.

Figure 7:
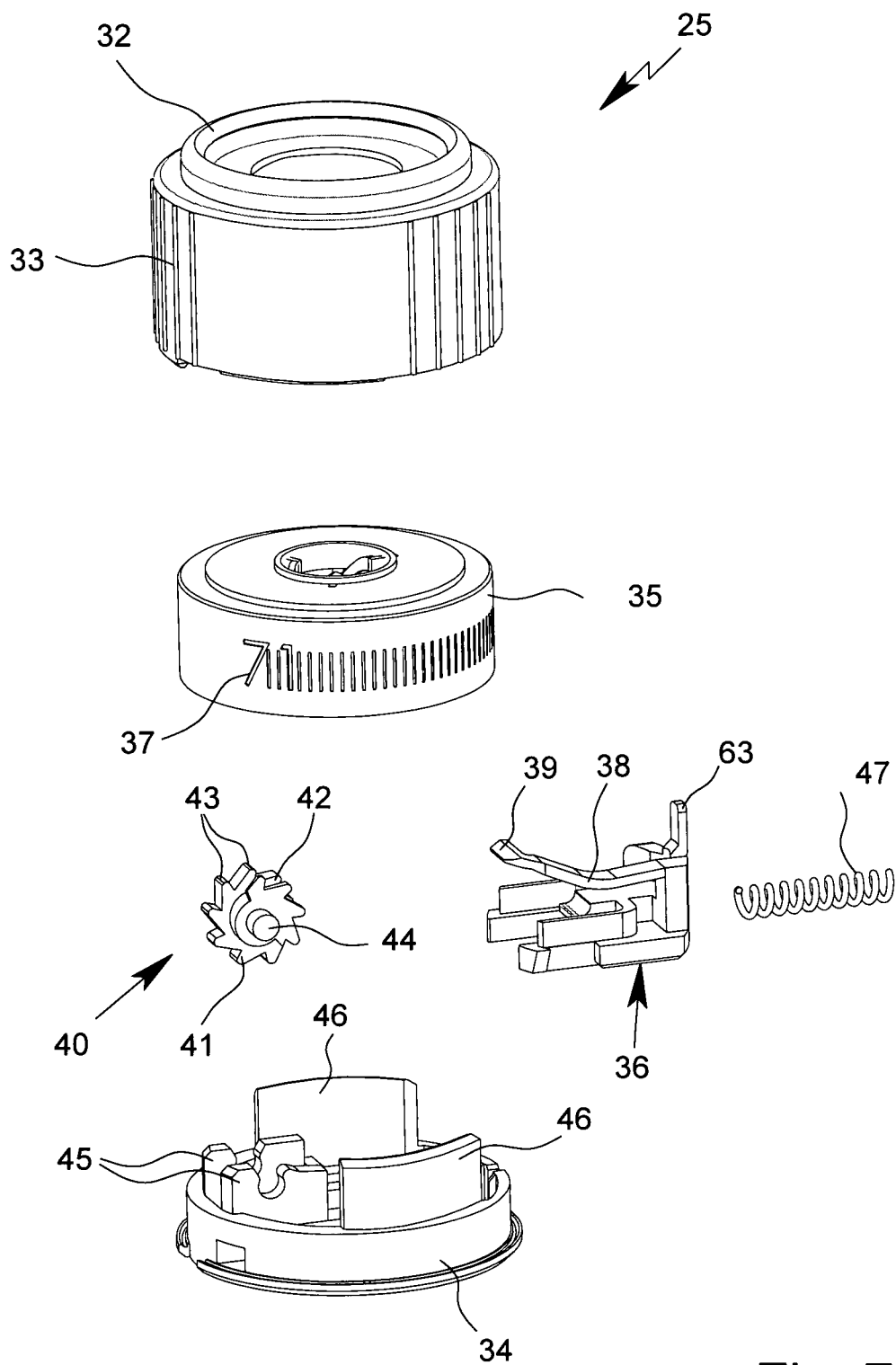
FIG. 7 a schematic exploded view of an indicator device according to a preferred embodiment of the present invention.

FIG. 7 shows in a schematic, exploded view the indicator device 25 according to the preferred embodiment of the present invention.

The indicator or its housing 31 comprises preferably an upper part 33 and a lower part 34.

Preferably, the upper part 33 holds or forms the gripping section 32.

The indicator device 25 comprises preferably an indicator element 35 and an associated actuation element 36 and/or a transmission 40 or gear 41 for indexing the indicator element 35 or for causing the indexing of the indicator element 35.

The indicator device 25 is for counting and/or indicating a number of uses performed or still possible with the respective or associated container 3. Preferably, the indicator element 35 comprises markings 37, such as one or more symbols, numbers, coloured or shaded areas or the like, for at least roughly indicating the number of uses already performed with or still possible with the respective container 3. In the present embodiment, the indicator element 35 is preferably rotatable and/or comprises a circumferential wall or outer surface with the at least one marking 37.

The indicator housing 31 comprises preferably a window 31a, in particular in the circumferential wall through the relevant marking 37 is visible for a user or patient, preferably through the housing part 18 which is in particular transparent.

The actuation element 36 comprises preferably an actuation arm 38 which, in turn, comprises preferably a free or actuation end 39, for direct or indirect actuation or indexing of the indicator element 35. Indexing means that the indicator element 35 is moved forward in increments or steps.

Preferred is an indirect actuation or driving so that the actuation element 36 or its arm 38 actuates or drives the indicator element 35 via a transmission 40. In the present embodiment, the transmission 40 results in a reduction and/or is realized as a worm device.

The indicator device 25 or transmission 40 comprises preferably a gear 41 and/or a worm 42. Most preferably, the worm 42 is directly formed by the gear 41 so that the gear 41 forms a worm gear and preferably comprises radially protruding teeth 43 in which at least one convolution of the worm 42 is formed (compare the horizontal or axial sections of the mounted indicator device 25 shown in FIGS. 8 and 9).

The gear 41 comprises preferably an axle, in particular one or more axle sections 44 which may axially protrude on opposite sides as realized in the present embodiment.

The actuation element 36 causes a rotation of the gear 41 around an axis preferably perpendicular to the direction of movement of the actuation element 36, the axis preferably being arranged in a horizontal plane identical or parallel to the plane given by the movement of the actuation element 36.

The gear 41 is rotatably held preferably by the housing 31 or lower housing part 34, preferably by two bearing sections 45 of the lower part 34. Preferably, the bearing sections 45 comprises recesses for rotatably holding the axle sections 44. However, other constructional solutions are possible as well.

The housing 31 or lower part 34 bears preferably the indicator element 35 such that it can rotate. In the present embodiment, the lower part 34 comprises preferably two bearing portions 46 arranged on opposite radial sides and axially protruding for rotatably bearing the indicator element 35. The actuation element 35 and/or transmission 40 are preferably arranged at least essentially in between the bearing portions 46.

The indicator device 25 comprises preferably an actuation spring 47, in particular for biasing the actuation element 36 into a preferred direction and/or for driving the indicator element 35.

Figure 8:
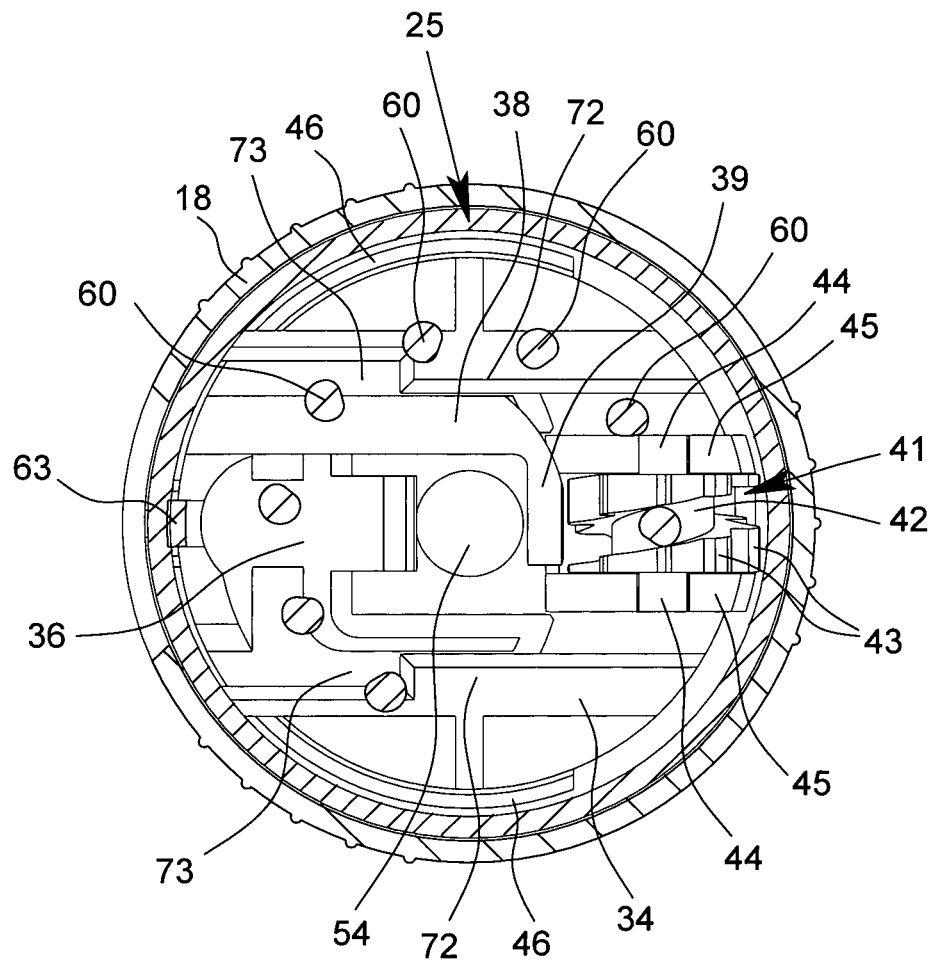
FIG. 8 an axial section of the indicator device in an actuated state.

FIG. 8 shows in a horizontal or axial section the mounted indicator device 25 in an actuated state where the actuation element 36 has been moved or pushed sidewards, namely starting from the first position shown in FIGS. 3 to 6 towards the left into a second position which is shown in FIG. 8.

Figure 9:
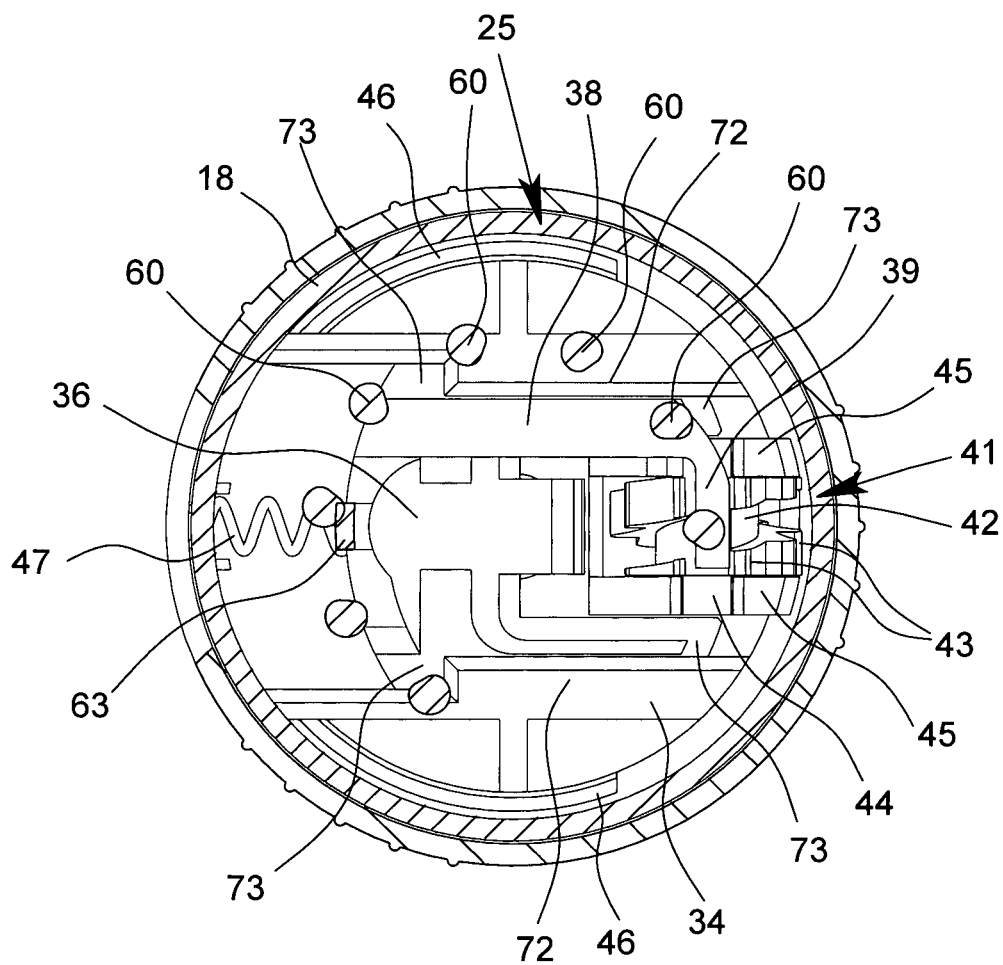
FIG. 9 an axial section of the indicator device in a locked state.

FIG. 9 shows in a similar section as FIG. 8 the indicator device 25 in a locked state where the actuation element 36 is in a locked, third position.

It can been seen from FIGS. 8 and 9 that protrusions 60 of the indicator element 35 (not shown in FIGS. 8 and 9) extend axially, wherein always at least one protrusion 60 is caught in the worm 42 so that a worm drive is formed between the gear 41 and the indicator element 35. Thus, any rotation of gear 41 is transformed in a reduced rotation of the indicator element 35. Further, a permanent engagement between the gear 41 and the indicator element 35, more precisely between at least one protrusion 60 and the worm 42, is ensured. However, other constructional solutions or couplings between the gear 41 and the indicator element 35 are possible.

Figure 10:
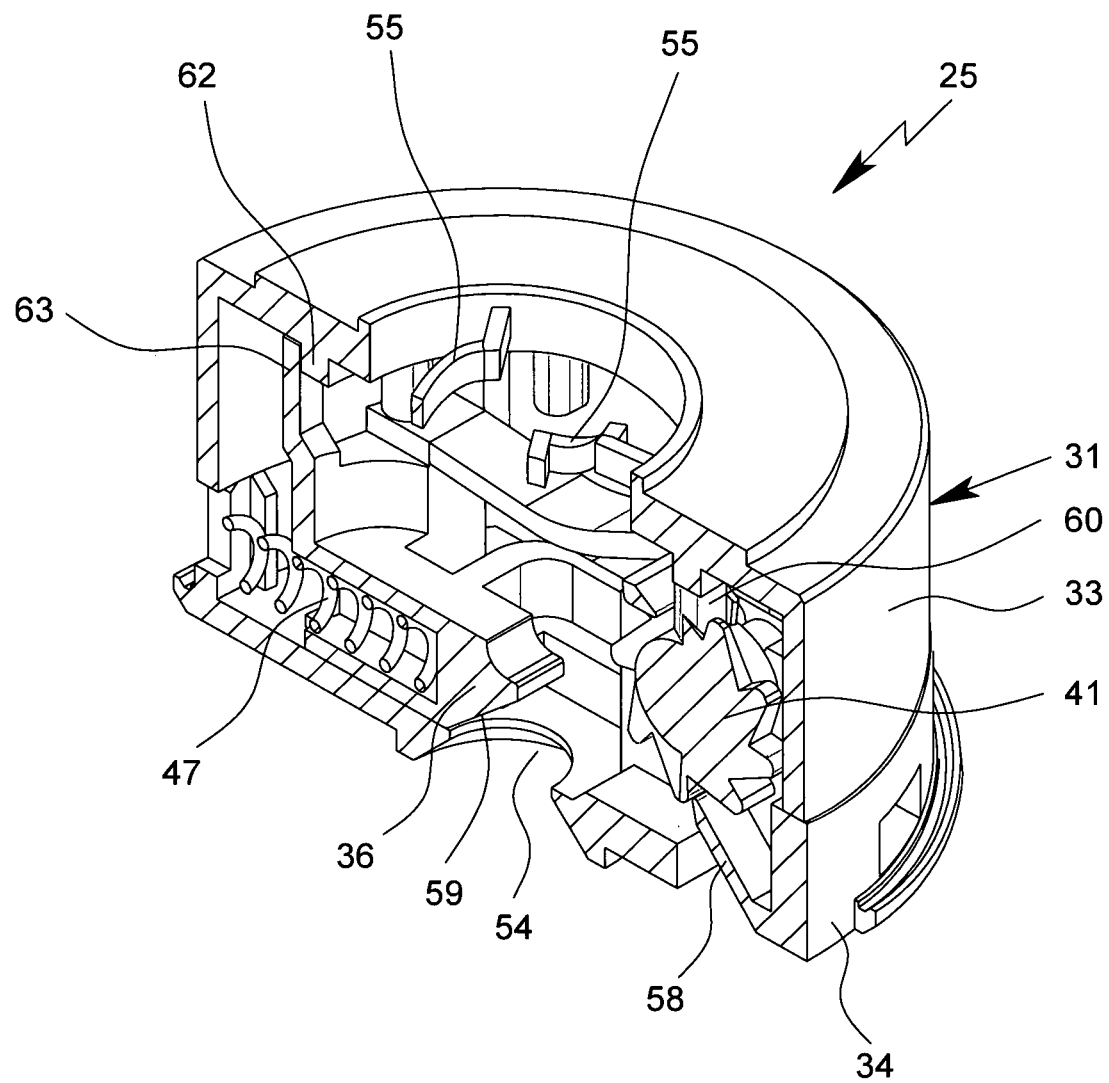
FIG. 10 a perspective section of the indicator device in an actuated state.
Figure 11:
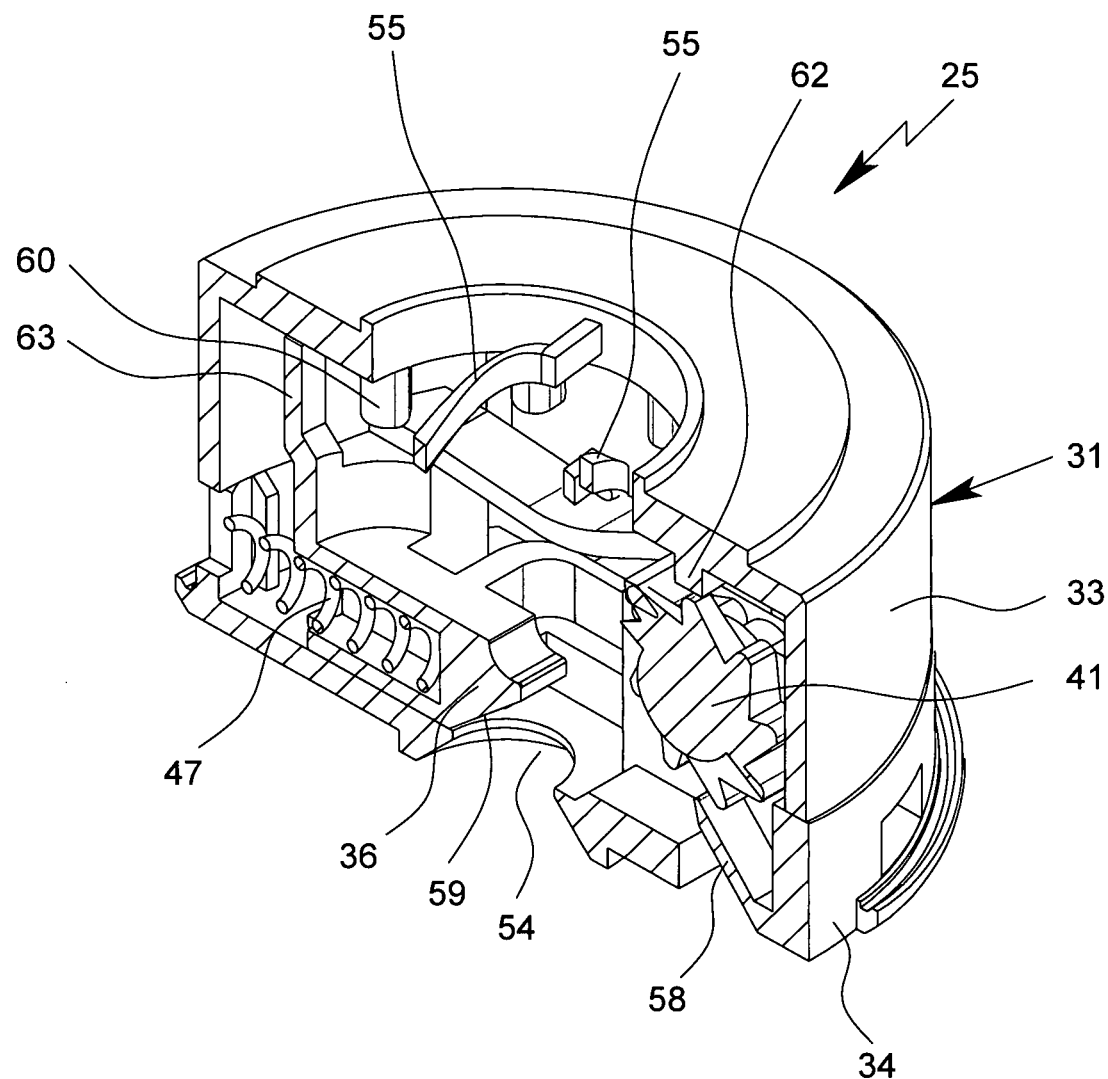
FIG. 11 a perspective section of the indicator device in an released state.

FIG. 10 shows the mounted indicator device 25 in a perspective section in the initial, first position and state. FIG. 11 shows the indicator device 25 in a similar perspective section, but with released actuation element 36, i.e. just before the locked state is reached.

Preferably, the transmission 40 or gear 41 forms a worm (helical groove) 42 with at least one convolution, preferably a with about 1.5 or more convolutions, so that always at least one engaging element of the indicator element 35 or of any other transmission component, in particular the inwardly or axially projecting protrusion 60, engages in the worm 42. Thus, rotation of the gear 41 around its preferably transversal axis results in a rotation of the indicator element 35 around its preferably longitudinally oriented rotation axis. However, other constructional solutions are possible as well.

Preferably, the teeth 43 are relatively long and/or extend radially sufficiently so that the protrusions are securely guided within the convolutions of the worm 42, in between the teeth 43, and that the actuation portion 39 can still move in radial direction between the protrusion 60 engaging into the worm 42 and the gear 41 in order to actuate or rotate the gear 41 in the desired manner. For this purpose, the actuation portion 39 may engage into respectively deep cut outs between the teeth 43 in order to be able to move below the respective projection 60.

The indicator device 25 comprises preferably a piercing part 48 (compare FIGS. 3 to 6).

The piercing part 48 is arranged within the indicator device 25 or its housing 31.

The piercing part 48 is preferably axially moveable.

The piercing part 48 is preferably moveable such that it can protrude towards the container 3 and/or can open an aeration opening, preferably the venting hole 23, of the container 3, in particular by breaking or piercing a foil 50 covering the venting hole 23.

In the present embodiment, the piecing element 48 comprises preferably an opening end or tip 49 which can open or pierce the foil 50 covering the container base 21, in particular an indention 51 formed in the container 3 or its base 21. Preferably, the indention 51 comprises a break through which forms the venting hole 23. However, other constructional solutions are possible as well.

Figure 12:
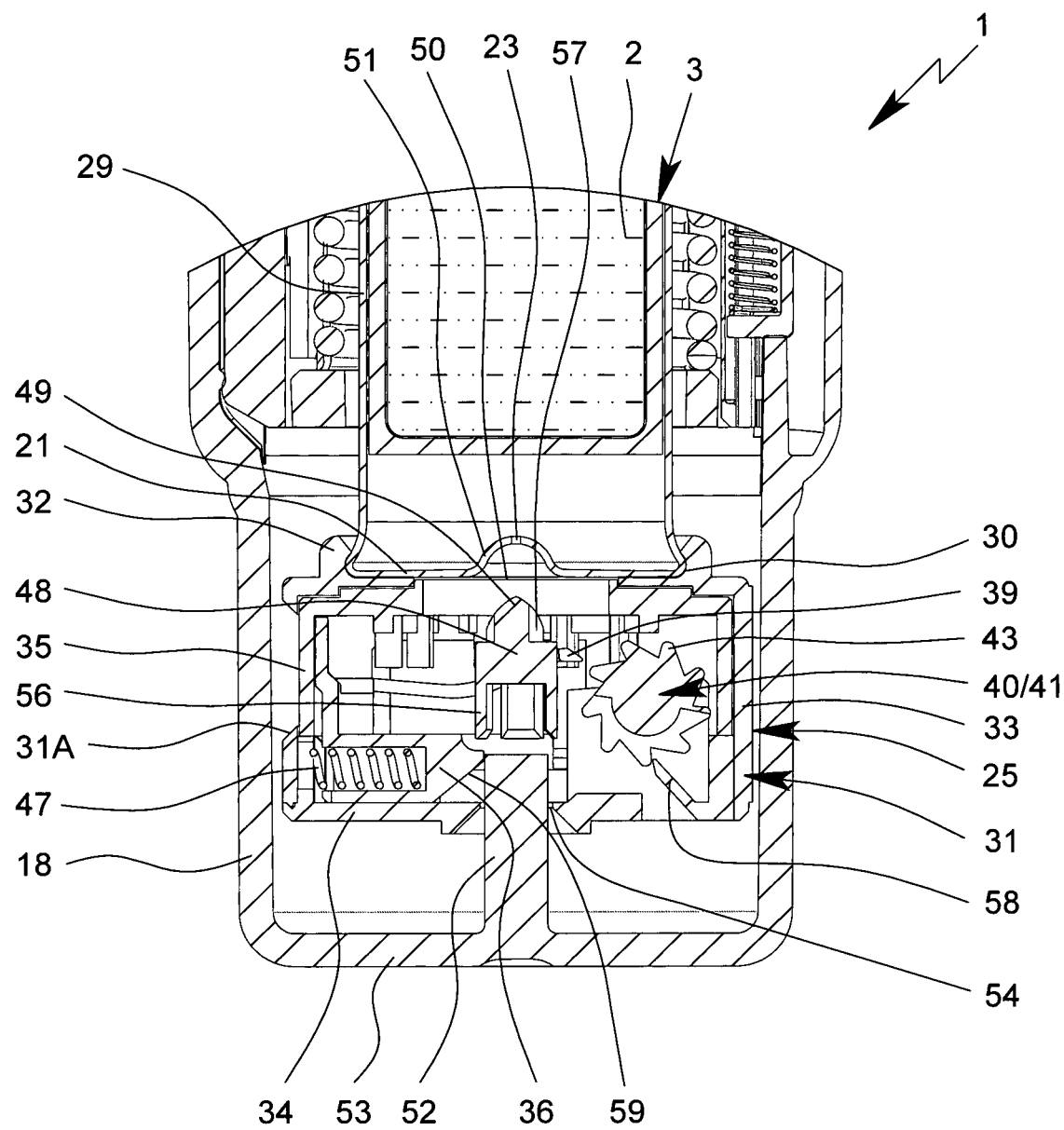
FIG. 12 a partial enlargement of the nebulizer similar to FIG. 4, but in a partially tensioned state.

FIG. 12 shows in a partial enlargement similar to FIG. 4 a lower portion of the nebulizer 1 in an intermediate state after partial tensioning. The indicator device 25 is in an actuated state as shown in FIG. 8 (second position).

The nebulizer 1 or housing part 18 comprises preferably a driving part 52 for driving or actuating the indicator device 25 when using the nebulizer 1, in particular for actuating the indicator device 25 in response to any tensioning of the nebulizer 1 and/or any (axial or stroke-like) movement of the container 3.

Preferably, the driving part 52 is arranged or formed in the housing part 18, in particular on the axial end face or bottom 53 of the housing part 18.

Preferably, the driving part 52 is arranged centrally and/or extends axially.

Preferably, the driving part 52 is at least substantially cylindrical and/or pin-like or bolt-like.

Preferably, the driving part 52 is held by the housing part 18 and/or integrally formed by the housing part 18.

In the preferred embodiment, the movement of the container 3 and, thus, of the indicator device 25 during the tensioning (downward movement in the drawings) and/or during pressurization and dispensing (upward movement in the drawings) and/or one or both of the respective end positions in the non-tensioned state and tensioned state, respectively, can be used for actuating the indicator device 25, i.e. for counting.

Preferably, the relative movement of the container 3 and/or indicator device 25 within the nebulizer 1, and more preferred the movement during dispensing, is used for actuating or triggering the indicator device 25 and/or counting.

When tensioning the nebulizer 1 and/or moving the indicator device 25 downwards, the driving part 25 enters or engages through an insertion opening 54 of the indicator device 25 or its housing 31, in particular axially.

Preferably, the driving part 52 and the insertion opening 54 are arranged centrally and/or axially aligned.

In the present embodiment, the driving part 52 actuates the actuation element 36, i.e. moves the actuation element 36 from an initial first position shown in FIGS. 3 to 6, to an actuated second position shown in FIG. 9.

Preferably, the actuation spring 47 biases the actuation element 36 into the first position.

In the present embodiment, the actuation element 36 is moveable back and forth between the first and second positions for indexing the indicator element 35, in particular for incrementally rotating the gear 41 in one direction to respectively drive the indicator element 35. As any rotation of gear 41 is transformed in a reduced rotation of the indicator element 35, thus every movement of the actuation element 36 from the first to the second position or vice versa results in a movement of the indicator element 35.

In the present embodiment, the actuation element 36 is moveable transversally, preferably perpendicularly, to the longitudinal or dispensing direction of the container 3 or nebulizer 1 and/or to the stroke movement of the container 3 and/or indicator device 25.

Preferably, the actuation element 36 is moved from the more central first position radially outwards to the second position, in particular against the force of the associated, preferably helical actuation spring 47 biasing the actuation element 36 in opposite direction.

In the second position, the actuation element 36 has been moved with its actuation arm 38 or actuation portion 39 out of engagement with gear 41 as indicated in FIGS. 8 and 12.

Figure 13:
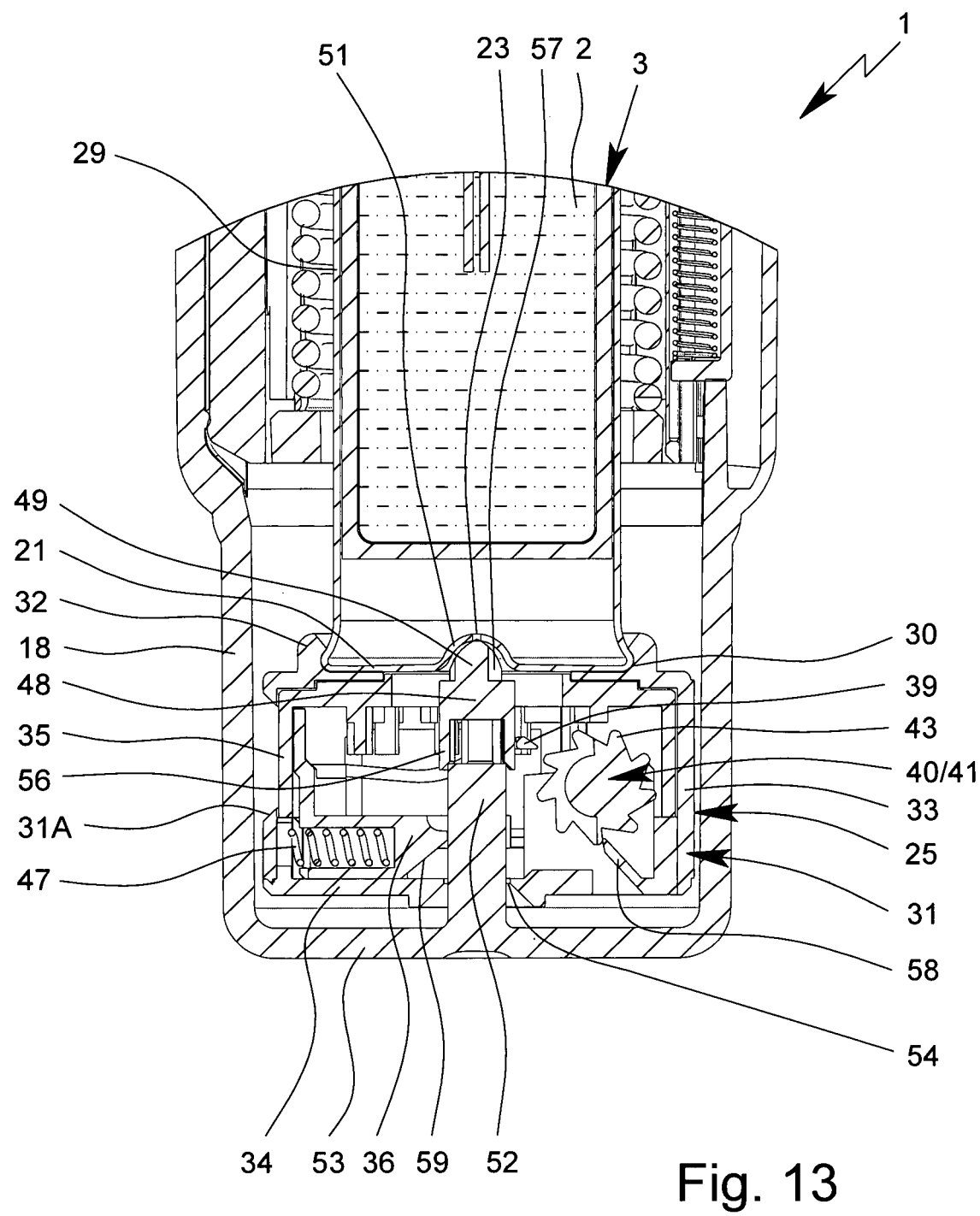
FIG. 13 a partial enlargement of the nebulizer similar to FIG. 4, but in a fully tensioned state.

FIG. 13 shows in a similar enlarged section as FIG. 12 the fully tensioned state.

In the (fully) tensioned state, the container 3, more precisely the aeration opening or venting hole 23, is opened at least when the nebulizer 1 is tensioned with a container 3 for the first time.

Preferably, the opening of the container 3 or venting hole 23 for aeration is realized by piercing or breaking, in particular of foil 50.

The opening or piercing can be effected directly by the driving part 52. Alternatively, the opening or piercing can be effected independently from the driving part 52, e.g. by means of the aeration spring 20 with the piercing element 22 similar to the embodiment shown in FIG. 2. Alternatively, as in the present embodiment, the opening or piercing can be achieved indirectly, preferably via the piercing part 48 which is preferably actuated by the driving part 52.

Preferably, the piercing part 48 is formed as separate part and/or provided by the indicator device 25 and/or arranged within the indicator device 25.

In the preferred embodiment, the piercing part 48 is held axially moveable by a support structure 55 of the indicator device 25, housing 31, upper part 32 and/or indicator element 35, as schematically indicated in FIGS. 10 and 11.

Preferably, the piercing part 48 and/or the support structure 55 are a one-piece-construction with a further part of the indicator devices 25, e.g. with the indicator element 35 or with the indicator housing 31, especially with the upper part 33 of the indicator housing 31.

Preferably, the piercing part 48, support structure 55 and the further part of the indicator device 25 are made of plastic in an injection molding process.

Preferably, the support structure 55 comprises flexible arms or ribs for holding the piercing part 48 axially moveable.

Alternatively the piercing part 48 can be constructed as separate, axially moveable part, which is optionally spring biased in the longitudinal or axial direction away from the container 3, so that the piercing tip 49 is retracted from the container 3 in the non-tensioned state.

It has to be noted that the piercing part 48 or its tip 49 is preferably received within the indicator device 25 or its housing 31, but can protrude outwards in the actuated state.

The opening or piercing can be repeated each time the nebulizer 1 is tensioned, i.e. each time when the container 3 reaches its end position in the tensioned state.

The piercing part 48 may be biased into its retracted or initial position shown in FIGS. 3 to 6, in particular by a preferably integrally formed biasing arm, spring or the like, preferably by the support structure 55.

The piercing part 48 may comprise a compensation portion, such as a flexible arm 56, for compensating any tolerances in the axial direction. Such tolerances can occur in particular due to variations during production, in particular variations of the length of the container 3 and/or other components, variations of the connections of the container 3 with the indicator device 25, variations of the length of the indicator device 25 or its housing 31, variations of the axial position of the container 3 within the holder 6, and the like. Thus, different distances between the free end of driving part 52 and the counter-face of the piercing part 48 can result. The construction is such that the driving part 52 and the piercing part 48 cooperate in any case such that the desired piercing is ensured.

The compensation portion allows axial compression—here by radial flexing of arms 56—when a predetermined axial force is exceeded in order to avoid any damage of the container 3 and/or any other component of the nebulizer 1. Thus, in the preferred embodiment the driving part 52 first moves the piercing part 48 towards the container base 21 into the piercing position and further axial movement of the driving part 52 is compensated by the compensation portion, preferably by the flexible arms 56 being spread radially outwards, giving way to the tip of the driving part 52 for entering a central recess in the piercing part 48 (on the side opposite to the piercing tip 49).

The piercing part 48 comprises preferably at least one axial channel, in particular one or more axially extending grooves 57 circumferentially distributed around the circumference of tip 49, in order to ensure unblocked aeration or venting even if the piercing part 48 stocks or stays in the foil 50 or piercing position.

Figure 14:
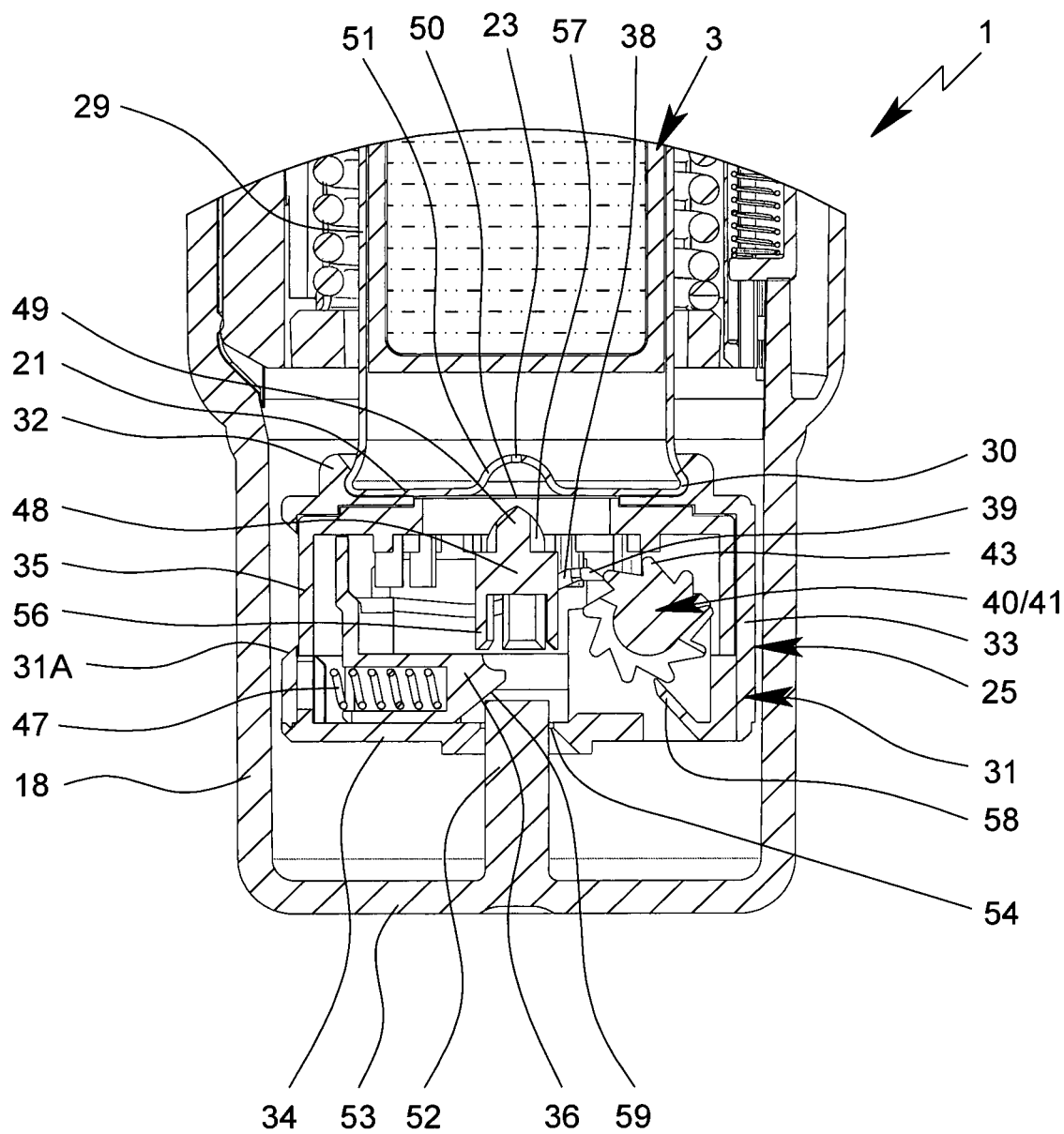
FIG. 14 a partial section of the nebulizer similar to FIG. 4, but in an intermediate state during a dispensing stroke.

FIG. 14 shows in a similar enlargement as FIGS. 4, 12 and 13 an intermediate state of the pressurization or dispensing process, i.e. when the container 3 has been moved partially upwards again. In this state, the driving part 52 has been withdrawn from the indicator device 25 or through the insertion opening 54 partially such that the actuation element 36 starts to return to its initial or first position due to the force of the actuation spring 47. Finally, after sufficient withdrawal of the driving part 52, the actuation element 36 returns into the first position shown in FIGS. 3 to 6 when the back movement is completed.

The back movement of the container 3 and/or of the actuation element 36 actuates preferably the indicator device 25 or gear 41 and/or is detected or counted. In particular, the actuation element 36 or its arm 38 or actuation portion 39 transmits the back movement or movement from the second to the first position to the transmission 40. In particular, this movement causes an incremental rotation of gear 41.

Thus, in the present embodiment, the movement of the container 3 and/or indicator device 25 within the nebulizer 1 during dispensing is preferably used for actuating or triggering the indicator device 25 and/or for counting.

In the present embodiment, the actuation arm 38 or its portion 39 abuts against one tooth 43 of gear 41 during the back movement and, thus, turns the gear 41 due to the back movement one step further, in the drawings in clockwise direction.

Preferably, the indicator device 25 comprises a ratchet 58 preventing any counter-rotation of the transmission 40 or gear 41. Into the present embodiment, the ratchet 58 is formed by a flexible arm extending from the housing 31, in particular lower housing part 34, and/or meshing with or engaging into the gear 41 or its teeth 43.

In the end position, i.e. in the non-tensioned state, the driving part 52 is preferably further or completely retracted from the indicator device 25, the indicator housing 31 and/or insertion opening 54 as shown in FIGS. 3 to 6.

The transmission 40 or gear 41 transforms the actuation, in particular the (backward) movement of the actuation element 36 or its arm 38/actuating portion 39, into an indexing of the indicator element 35. The transmission ratio or transmission function of the transmission 40 or gear 41 may be designed or constructed such that a reduction or non-linear driving or indexing is achieved. In the present embodiment, the transmission 40 or gear 41 forms preferably a worm drive for achieving a desired reduction.

The movement of the actuation element 36—in particular from the first position to the second position—results in that the actuation arm 38 or its actuation portion 39 are moved out of engagement with the gear 41, in particular can be pulled over the next tooth 43. Hereby, the arm 38 is flexed out. The subsequent movement in opposite direction, i.e. the back movement or movement from the second to the first position, results in that the actuation arm 38 or its actuation portion 39 contacts the next tooth 41 and can transmit the at least essential linear movement of the arm 38, more precisely the preferably linear movement of the actuation element 36, into a rotation of the gear 41, more precisely in an indexing of gear 41 by preferably one tooth 43.

Preferably, the teeth 43 are asymmetrical, i.e. comprise differently inclined shoulders on one side and the other side in order to facilitate and/or ensure the incremental actuation and movement in one rotational direction by the back and forth movement and engagement of the actuation arm 38.

Preferably, the actuation element 36 is linearly moveable and/or forms a sliding carriage.

Preferably, the actuation element 36 is supported and/or held moveably by the housing 31, in particular lower part 34 of the housing 31. However, other constructional solutions are possible as well.

The actuation spring 47 acts preferably between the housing 31 or lower part 34 on one hand and the actuation element 36 on the other hand.

In the present embodiment, the spring 47 is preferably already compressed and/or biased in the first position and/or biases the actuation element 36 such that it at least partially closes or blocks the insertion opening 54.

Preferably, the actuation element 36 comprises an inclined gliding surface 59 at its part projecting into or over the insertion opening 32 in the first position. This surface 59 is inclined such that the insertion of the driving part 52, i.e. its axial movement or abutment, is transformed into a transversal or radial movement of the actuation element 36.

Alternatively or additionally, such a surface 59 can also be formed at the driving part 52 to achieve the desired transformation of the axial movement into a transversal or radial movement by means of an inclined plane.

Therefore, the actuation or rotation of the transmission 40 or gear 41 is preferably effected by the force of the actuation spring 47 or any other pressure or energy store or spring means. This results in the advantage that no additional force is necessary for driving the indicator device 25 or its indicator element 35. Consequently, the pressurization and dispensing process is not disturbed.

Further, the triggering of the counting or actuation of the transmission 40/gear 41 is effected preferably by the pressurization or dispensing process or movement, i.e. during the actual dispensing of fluid 2, i.e. usually during actual use or inhalation.

The actuation spring 47 biases the actuation element 36 preferably towards closing the insertion opening 54.

Usually, the movement of the actuation element 36 is restricted so that it does not completely close the insertion opening 54 before the locked state is reached. This limitation is realized in the present embodiment preferably via a control means or portion 62 against which a control part 63 abuts in particular to restrict the back movement of the actuation element 36 at the first position.

The abutment is shown in particular in FIG. 10. However, other constructional solutions are possible as well.

After the number of uses of the nebulizer 1 with the container 3 has reached or exceeded a predetermined number of uses as detected or registered by the indicator device 25, a locked state is entered and the nebulizer 1 will be locked against further use with the current container 3 and/or the container 3 will be locked against further use with the nebulizer 1.

Figure 15:
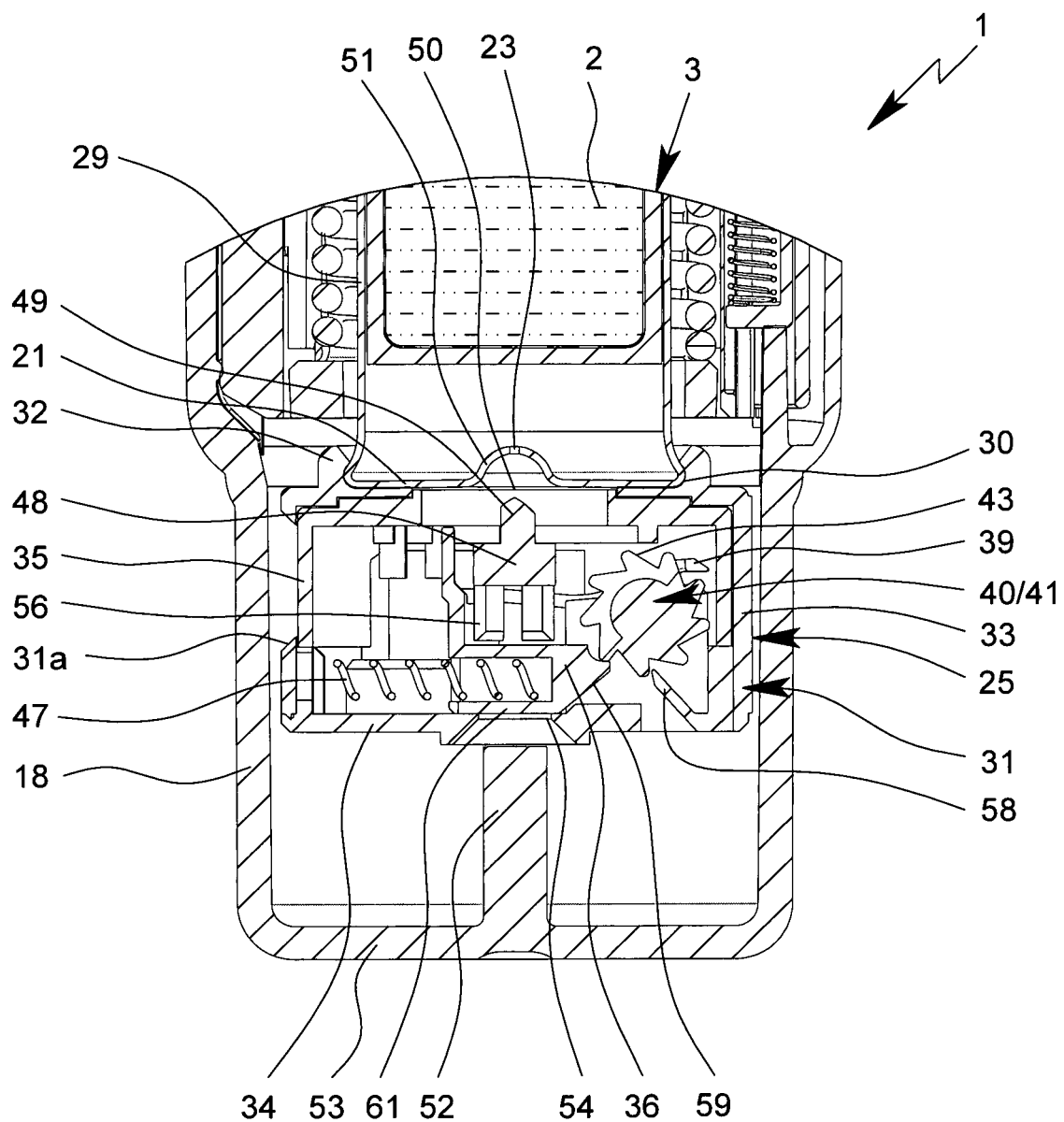
FIG. 15 a partial section of the nebulizer similar to FIG. 4, but with an indicator device of the container in a locked state.

In particular, the indicator device 25 comprises a blocking part 61 which blocks further use of the container 3 and/or closes or blocks the insertion opening 54 in the locked state as schematically shown in the schematic enlargement of FIG. 15 which shows a similar part as FIGS. 4 and 12 to 14. In this shown state, the container 3 has returned to its non-tensioned position and the driving part 52 has been retracted from the indicator device 25. During the last dispensing or pressurization process, the indicator device 25 has moved the indicator element 35 one step further and detected or registered that the predetermined number of uses has been reached or exceeded and, thus, that the locked state shall be entered.

In the present embodiment, the indicator element 35 comprises preferably a control portion 62 which releases the actuating element 36 for detection of the locked state which results in locking the nebulizer 1 or current container 3 against further use.

Preferably, the control portion 62 comprises a cut out or recess which allows or initiates movement of the blocking part 61 into a blocking position. Preferably, the blocking part 61 blocks or closes the insertion opening 54 in the blocking position, i.e. in the locked state. Preferably the control portion 62 is a wall or ridge on the inside of the rotatable indicator element 35.

Preferably, the blocking part 61 is integrated into the indicator device 25 or its housing 31.

The blocking part 61 is preferably moveable transversally or perpendicular to the longitudinal or dispensing direction of the container or nebulizer 1 and/or of the direction of stroke movement of the container 3.

Preferably, the blocking part 61 blocks the actuation or insertion movement of the driving part 52, in particular relative to the indicator device 25 and/or (sufficient) insertion of the driving part 52.

Preferably, the blocking part 61 is linearly moveable and/or formed by a sliding carriage. However, other constructional solutions are possible as well.

Preferably, the blocking part 61 is biased into its blocking position, in the present embodiment preferably by actuation spring 47 or any other suitable biasing means.

Preferably, the blocking part 61 closes or blocks the insertion opening 54 of the indicator device 25 after the last dose of fluid 2 has been dispensed and when the locked state has been entered or detected. This detection is preferably realized in that the blocking part 61 or any associated component, such as control part 63, can pass the control portion 62 in the locked state, most preferably by spring force, in particular by the force of actuation spring 47 or the like, as schematically shown in FIG. 11.

Preferably, the blocking part 61 is connected with or formed by the actuation element 36 or vice versa. Most preferably, the blocking part 61 forms a wall or side, preferably flat side, of the actuation element 36. However, other constructional solutions are possible as well.

In the present embodiment, the actuation element 36 can move in the locked state from the first position into the third position, i.e. preferably in the opposite direction than the movement into the second position.

In the present embodiment, the actuation element 36 can close the insertion opening 54 preferably completely in the third position (blocking position).

With other words, the blocking position of the blocking part 61 corresponds preferably to the third position of the actuation element 36.

In the locked state or third position, the actuation element 36 has moved with the actuation arm 38 or its portion 39 further in the actuation direction so that the actuation portion 39 has passed the previous tooth 43 in the rotation direction of gear 41 as indicated in FIG. 15.

Preferably, the actuation element 36 is constructed to block further use of the container 3 in the locked state or third position (blocking position).

Preferably, the actuation element 36 is moveable back and forth between the first and second position for indexing the indicator element 35 and is moveable into a third position to block further use of the container 3 in the locked state.

The above and the following description and features apply preferably as well or additionally for a modified embodiment described later with regard to FIGS. 19 and 20.

In particular, the closed indicator device 25 or blocking part 61 results in particular in that the container 3 cannot move inside the closed housing of the nebulizer 1 in the stroke-like fashion as previously described and as required for normal or further use so that normal use is prevented.

Figure 16:
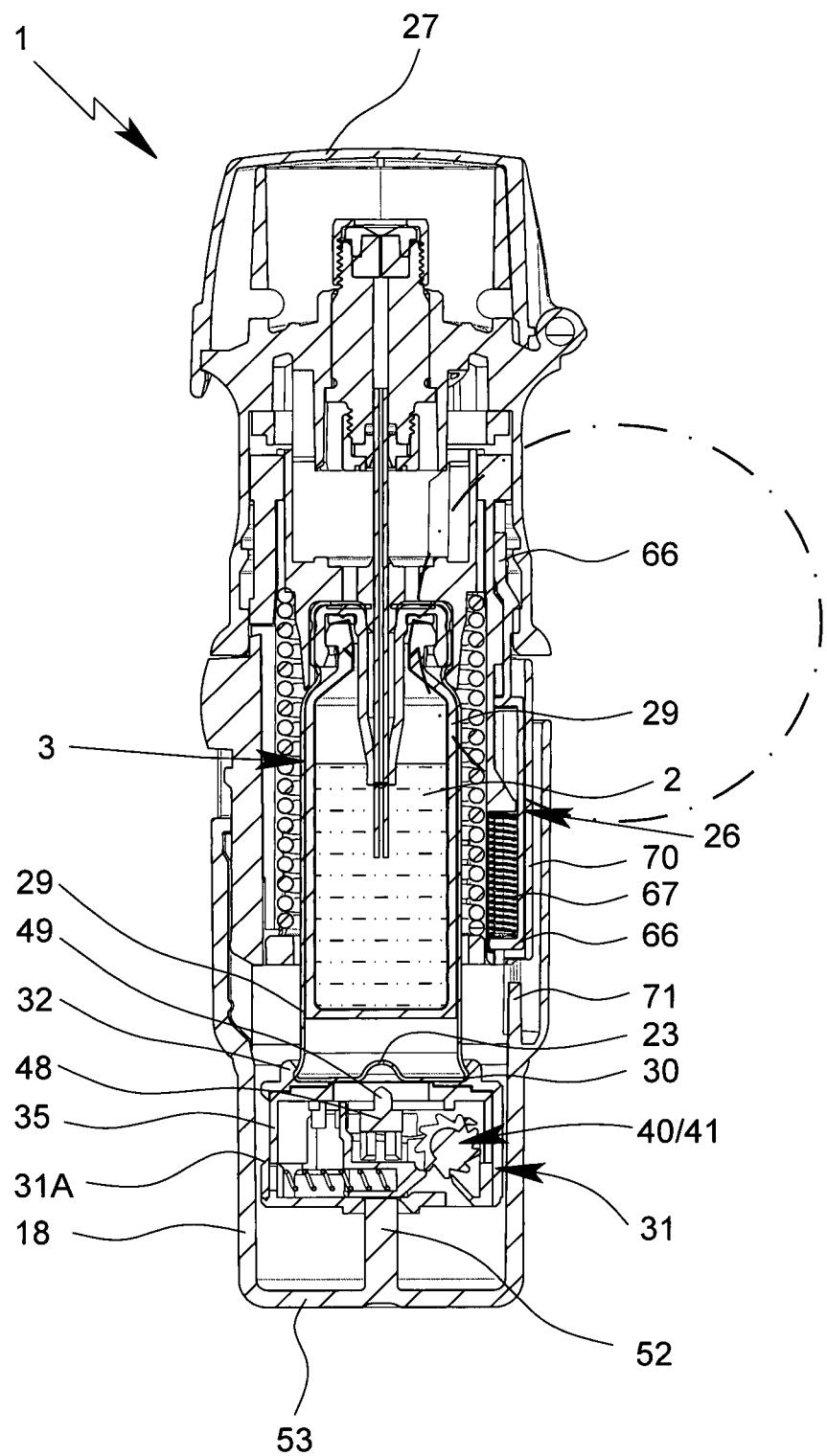
FIG. 16 a schematic section of the nebulizer in the locked state after next tensioning with partially opened housing part and with locked locking device.

In particular, the locking of the indicator device 25 or insertion opening 54 results in that the nebulizer 1 or housing part 18 is at least partially opened when the nebulizer 1 is tensioned once more or when it is partially tensioned. FIG. 16 shows this state (partially tensioned nebulizer 1 with partially opened housing part 18) in a schematic, longitudinal section of the nebulizer 1. During the tensioning process the container 3 is moving downwardly together with the indicator device 25. Starting from the non-tensioned state (upper position of the container 3), the indicator device 25 abuts soon with its blocking part 61/actuating element 36 against the member usually actuating the indicator device 25, here the driving part 52, so that a further usual downward movement is not possible.

In particular, the blocking part 61 restricts the axial moveability of the container 3 in the nebulizer 1 in the locked state, preferably by preventing the driving part 52 from insertion into the indicator device 25 or restricting its insertion in the locked state. Due to the force applied when tensioning the nebulizer 1 and due to the resulting axial force in the movement of the container 3, the housing part 18 will be moved outwards or relative to the nebulizer 1, inner part 17 or upper part 16 together with the container 3 and indicator device 25 during the further tensioning movement in the axial direction in the locked state.

The above common downward movement of container 3, indicator device 25 and housing part 18 is possible due to a respectively constructed fastening of the housing part 18 at the nebulizer 1. In particular, the retaining force is selected or set such that it can be overcome by the downward movement of the container 3.

In the present embodiment, the retaining element 19 engages with a retaining nose 64 in a respective retaining recess 65 in the housing part 18 or vice versa. Thus, substantially an undercut or indention can be realized. However, the abutting shoulders which extend at least essentially radially of the nose 64 on one hand and the recess 65 on the other hand are slightly inclined, preferably by about 1° to 5° to the radial plane such that the axial force of the tensioning process can overcome the retaining force provided by the engagement of the nose 64 into the recess 65 so that the retaining element 19 is flexed radially and the retaining engagement is overcome. Consequently, the housing part 18 is moved downwardly as well and, thus, is pushed at least partly from the nebulizer 1 or separated from the upper housing part 16 and/or pushed from the inner part 17.

This pushing or axial displacement of the housing part 18 or any other opening of the nebulizer 1 results preferably in that the nebulizer 1 is locked against further use by means of the locking device 26. Therefore, the indicator device 25 or its blocking part 61 effects indirectly via the opening of the nebulizer 1 the desired locking of the nebulizer 1 in the locked state.

In the preferred embodiment, the locking device 26 blocks tensioning of the nebulizer 1 in the locked state.

Preferably, the locking device 26 comprises a moveable locking element 66 and an associated locking spring 67. The locking element 66 is preferably axially moveable between a locked position and an unlocked position. The locking element 66 is preferably biased into a locking position/the locked position by the locking spring 67.

Figure 17:
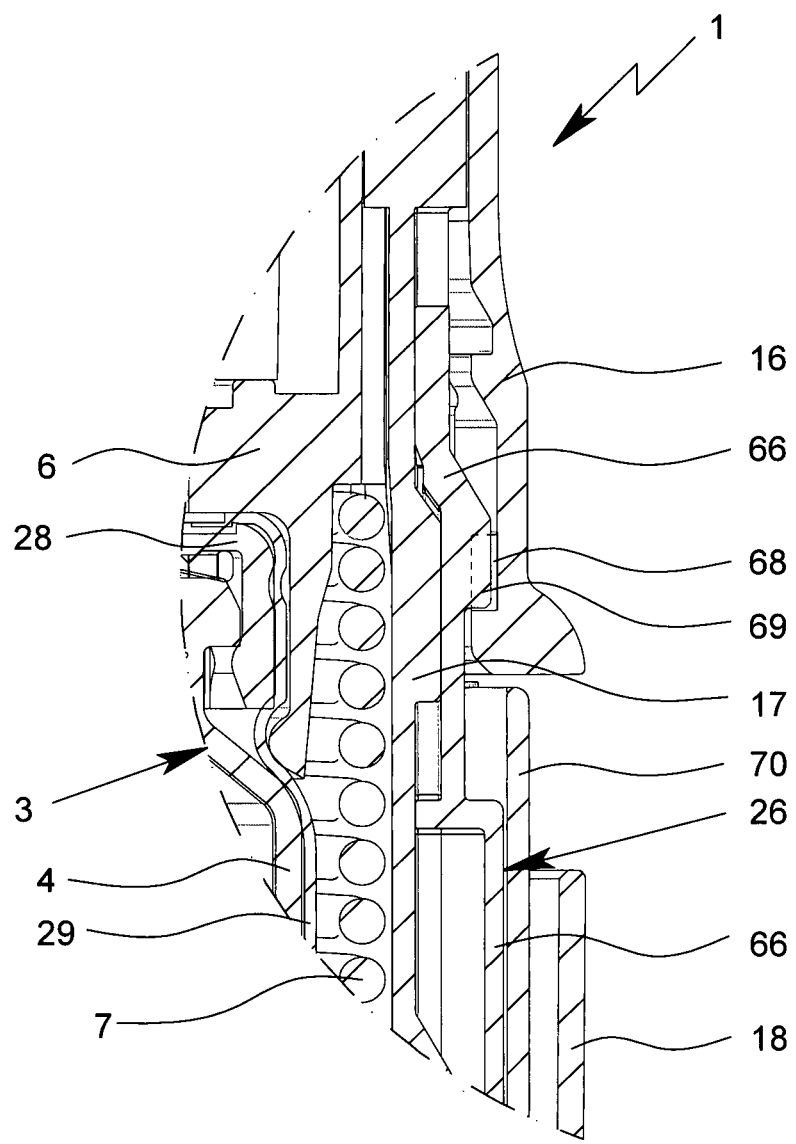
FIG. 17 a partial enlargement of the encircled part of FIG. 13.

In the locked position, the locking element 66 is preferably in its lower axial position shown in FIG. 16. FIG. 17 shows an enlargement of the encircled area of FIG. 16.

In the locked position, the locking element 66 blocks rotation of the inner part 17 relative to the outer part 16 and, thus, blocks (further) tensioning of the nebulizer 1. This is preferably achieved in the present embodiment in that the locking element 66 moves or engages preferably (only) axially into a respective pocket 68 formed in the upper part 16 such that said relative rotation is blocked. In particular, the locking element 66 engages with an engagement portion 69 into the respective recess or pocket 68 such that any further rotation and/or back rotation is prevented. However, other constructional solutions are possible as well.

Preferably, the engagement portion 69 protrudes radially and/or is at least essentially rib-like.

Figure 21:
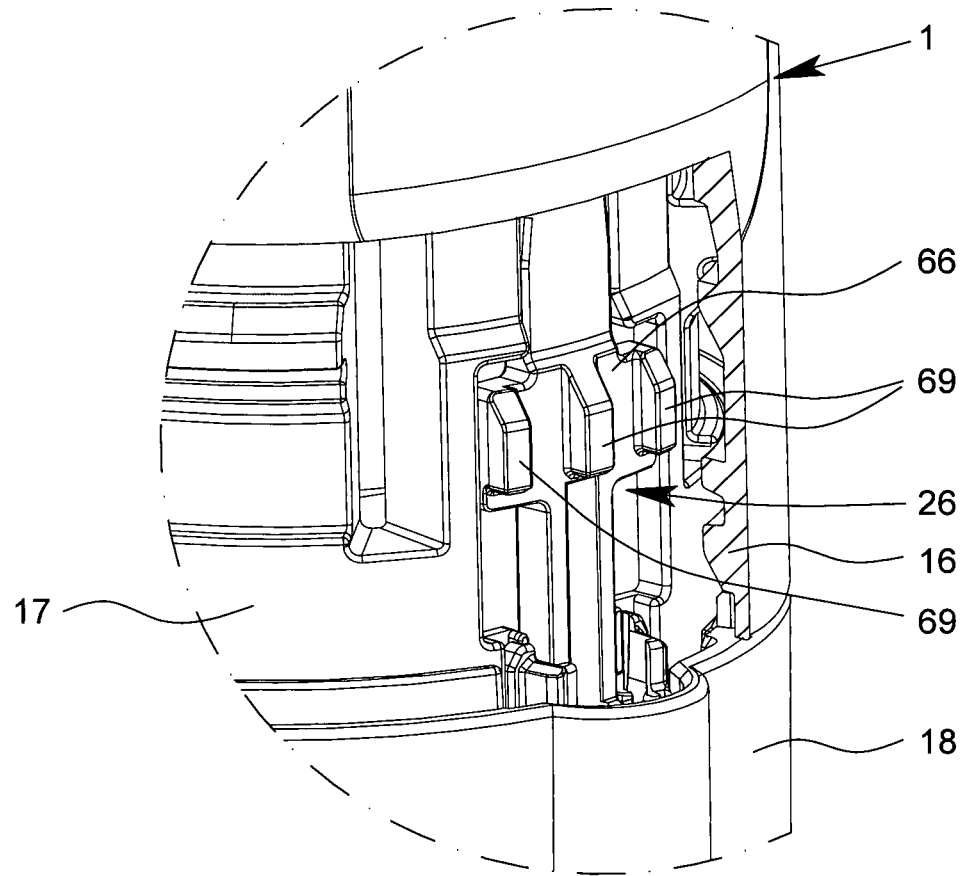
FIG. 21 a schematic side view of the nebulizer in the area of the encircled part of FIG. 16, but in an unlocked position and with partially opened upper housing part.

In the present embodiment, the locking element 66 comprises preferably multiple or three engagement portions 69 as shown in FIG. 21 which is a schematic side view of the nebulizer 1 in the region of the encircled part of FIG. 16 with opened or cut-away upper housing part 16. However, FIG. 21 shows the locking element 66 in its unlocked or upper position.

The engagement portions 69 extend preferably parallel to each other and/or in axial or actuation direction.

The engagement portions 69 are preferably rib-like and/or protrude radially and/or outwardly.

The locking element 66 together with the engagement portion(s) 69 is preferably formed by one-piece and/or as an integral or rigid part and/or made preferably of plastics.

Figure 22:
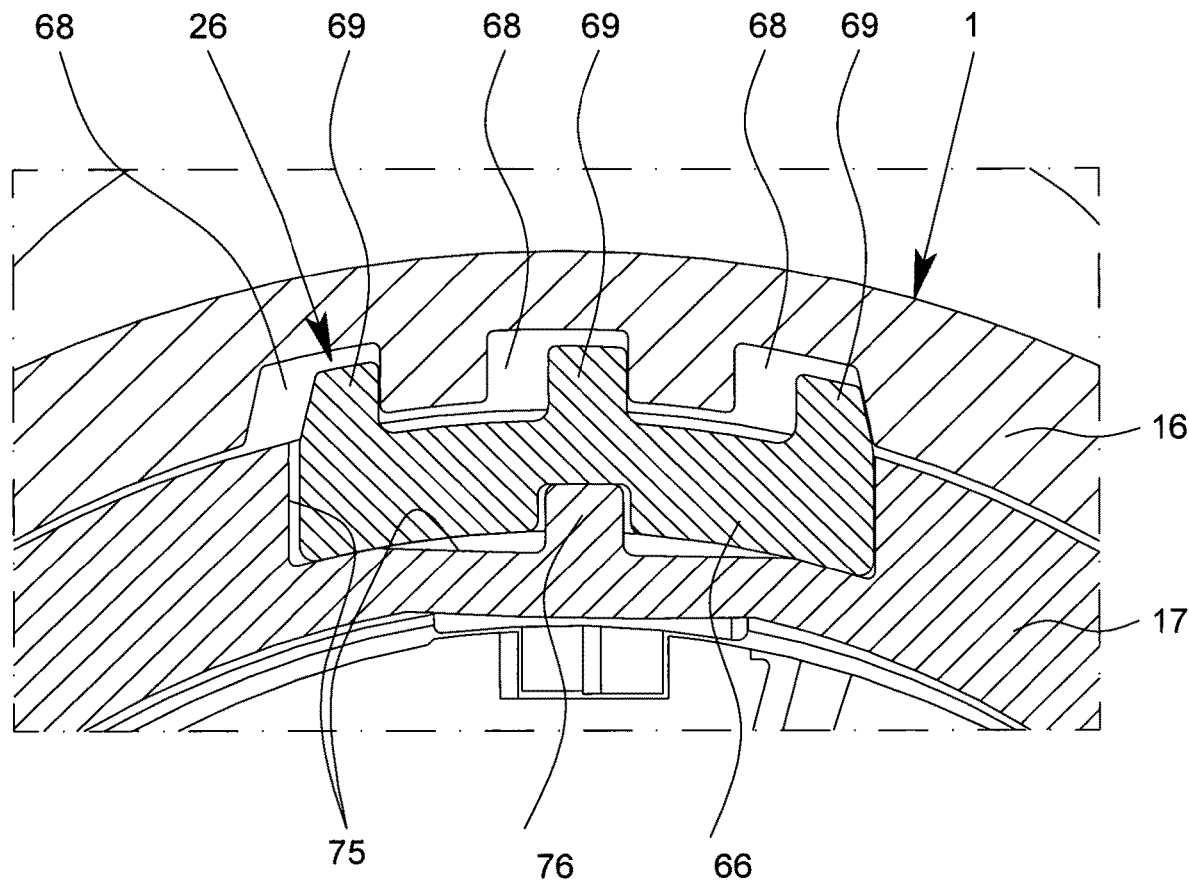
FIG. 22 a schematic partial section of the locking device in the locking position shown in FIGS. 16 and 17 in a radial plane.

FIG. 22 shows in a schematic radial section the engagement of the locking device 26 or its locking element 66 in the locked state or position, i.e. the rotational blocking, of the nebulizer 1, in particular of the inner part 17 and/or lower housing part 18 relative to the upper or outer housing part 16.

In particular, in the locked state the engagement portions 69 engage or protrude into separate or corresponding pockets 68 formed at or by (the inner side of) the housing part 16 of the nebulizer 1. However, other constructional solutions are possible as well.

The locking element 66 is preferably guided by the inner part 17 and/or in a respective groove 75 and/or by a preferably rib-like protrusion 76 or the like, as schematically indicated in FIG. 22, such that the locking element 66 is preferably only axially moveable. However, other constructional solutions are possible as well.

The locking device 26, in particular the locking element 66 and the locking spring 67, are preferably arranged and/or supported by the inner part 17 and/or extend between the inner part 17 and upper part 16.

The nebulizer 1, inner part 17 or locking device 26 comprises preferably a cover 70 covering the locking device 26 at least on the periphery of the lower part 17b of the inner part 17 in order to prevent or at least complicate any undesired manipulation of the locking device 26 or locking element 66 by a user or patient.

Preferably, the locking device 26 or locking element 66 is locking relative rotation or further rotation before the complete tensioned state or position is reached, i.e. preferably in an intermediate position, most preferably in the second half of the total rotation angle necessary for tensioning the nebulizer 1 by turning the lower housing part 18 relative to the upper housing part 16.

This intermediate blocking has the advantage that it is preferably not possible to fully actuate the nebulizer 1 as it is not possible to reach complete tensioning and, thus, the gear or transmission transforming the relative rotation into the axial stroke of the holder 6 actually holds the holder 6 in the intermediate position and does not allow any axial back movement into the upper, non-tensioned position.

However, it is also possible that the locking device 26 locks the nebulizer 1 against further tensioning after the complete tensioned state has been reached.

Alternatively or additionally, it is also possible that the locking device 26 or its locking element 66 locks the release of the spring 7 or holder 6 to dispense the fluid 2, in particular by locking any depression of blocking element 8 and, thus, blocking the release. However, other constructional solutions are possible as well.

Generally, the locking device 26 or its locking element 66 can be adapted to block additionally the actuation of the nebulizer 1 or block triggering the nebulization of a dose of the fluid 2 or block the depression of the blocking element 8 or any other actuation button or the like of the nebulizer 1. This may form an additional measure to block further use of the nebulizer 1 in the locked state.

Preferably, the nebulizer 1 or upper part 16 may be enforced by one or more metallic inserts or enforcement elements, which may be ring-like and/or may extend in circumferential direction and/or may be arranged adjacent to or around the pocket 68 and/or adjacent to the lower or free end of the upper part 16.

Figure 18:
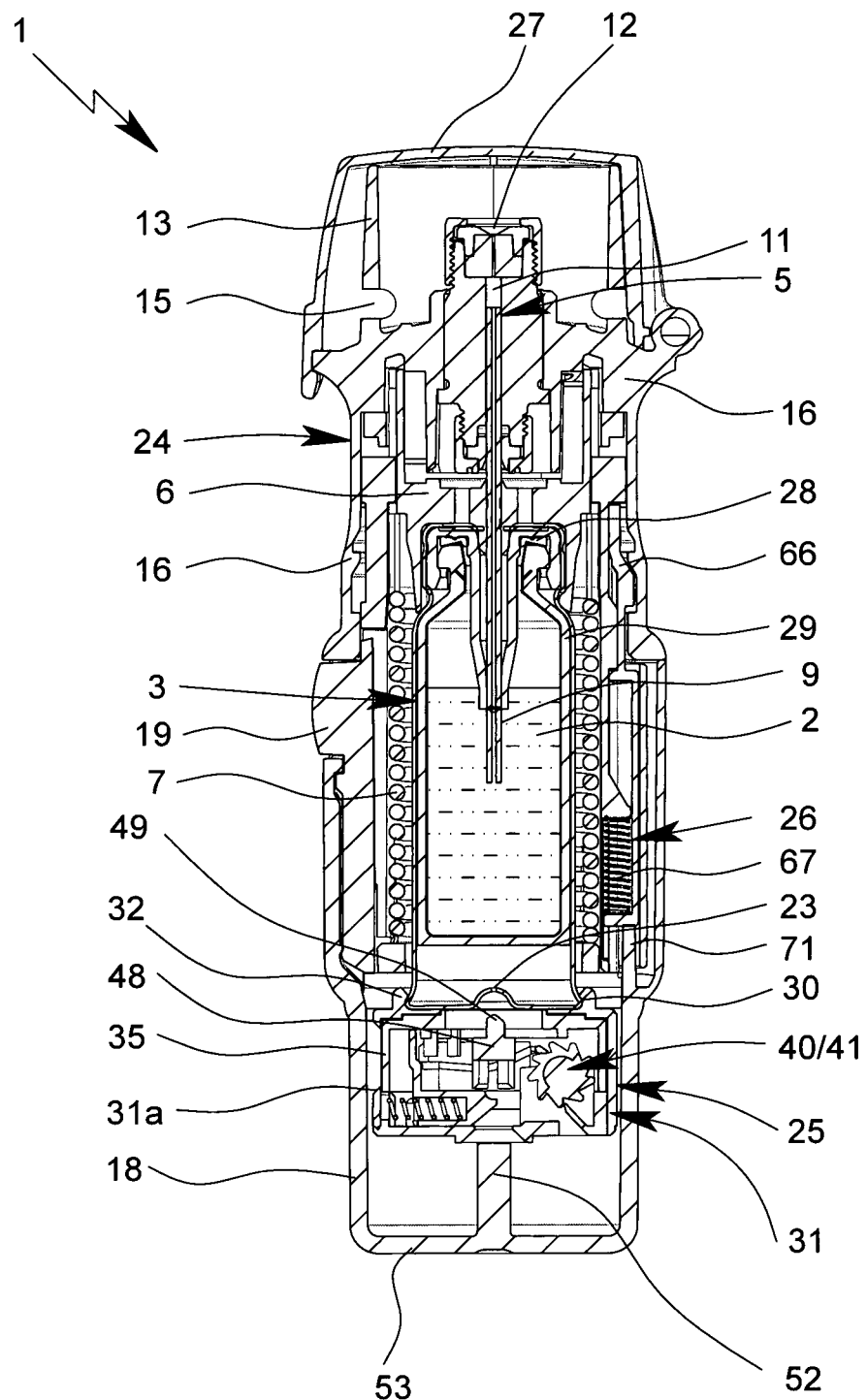
FIG. 18 a schematic section of the nebulizer similar to FIG. 3 with unlocked locking device.

FIG. 18 shows the nebulizer 1 in a similar schematic section as FIG. 16, however with the locking device 26 in the unlocked position, i.e. the locking element 66 in the upper position. The locking device 26 or locking element 66 is brought into this position or unlocked preferably only by closing the nebulizer 1, in particular by the housing part 18 in the completely attached or closed position.

In the shown embodiment, the housing part 18 comprises a preferably finger-like and/or axially extending actuator 71 which extends into the locking device 66 and/or into the cover 70 and/or axially abuts and/or pushes the locking element 66 into its unlocking position (upper position), as shown in FIG. 18. Thus, only the completely closed nebulizer 1 or housing part 18 unlocks the locking device 26 and, thus, unlocks the nebulizer 1.

The actuator 71 is preferably arranged within the housing part 18 so that any manipulation is not possible or at least complicated.

When the nebulizer 1 is in the locked state and, preferably when the nebulizer 1 or its housing part 18 has been opened partially by the last tensioning process, any further use of the nebulizer 1 with the container 3 and the indicator device 25 in its locked state is not possible. The locking device 26 locks preferably automatically. Preferably, the locking spring 67 biases the locking element 66 into the locking position, so that upon at least partial opening of the nebulizer 1 or (axial) displacement of its housing part 18, the locking device 26 or its locking element 66 can move and moves into the locking position.

Preferably, the locking element 66 is moveable (essentially or only) in the axial direction.

After replacement of the current container 3 with its locked indicator device 25 (blocking part 61 in the blocking position) against a new container 3 including a new or reset indicator device 25, the nebulizer 1 or its housing part 18 can be closed completely again. Thus, the nebulizer 1 or its locking device 26 can be or is unlocked again. Preferably, the actuator 71 pushes the locking element 66 back into its unlocking position.

Thus, the locking device 26 or locked state is reset or unlocked again, preferably by (completely) closing the nebulizer 1, its housing 24 or housing part 18, and the nebulizer 1 can be used with the new container 3 as previously.

In the shown embodiment, the locking element 66 is preferably formed by one single part. However, the locking device 26 may comprise multiple parts forming or containing the locking element 66.

Preferably, the container 3 is or has to be replaced in an at least partially tensioned state of the nebulizer 1, in particular such a tensioned state that complete closing of the nebulizer 1 or its housing 24 is not possible when the indicator device 25 is in the locked state or when the insertion opening 54 is closed.

Figure 24:
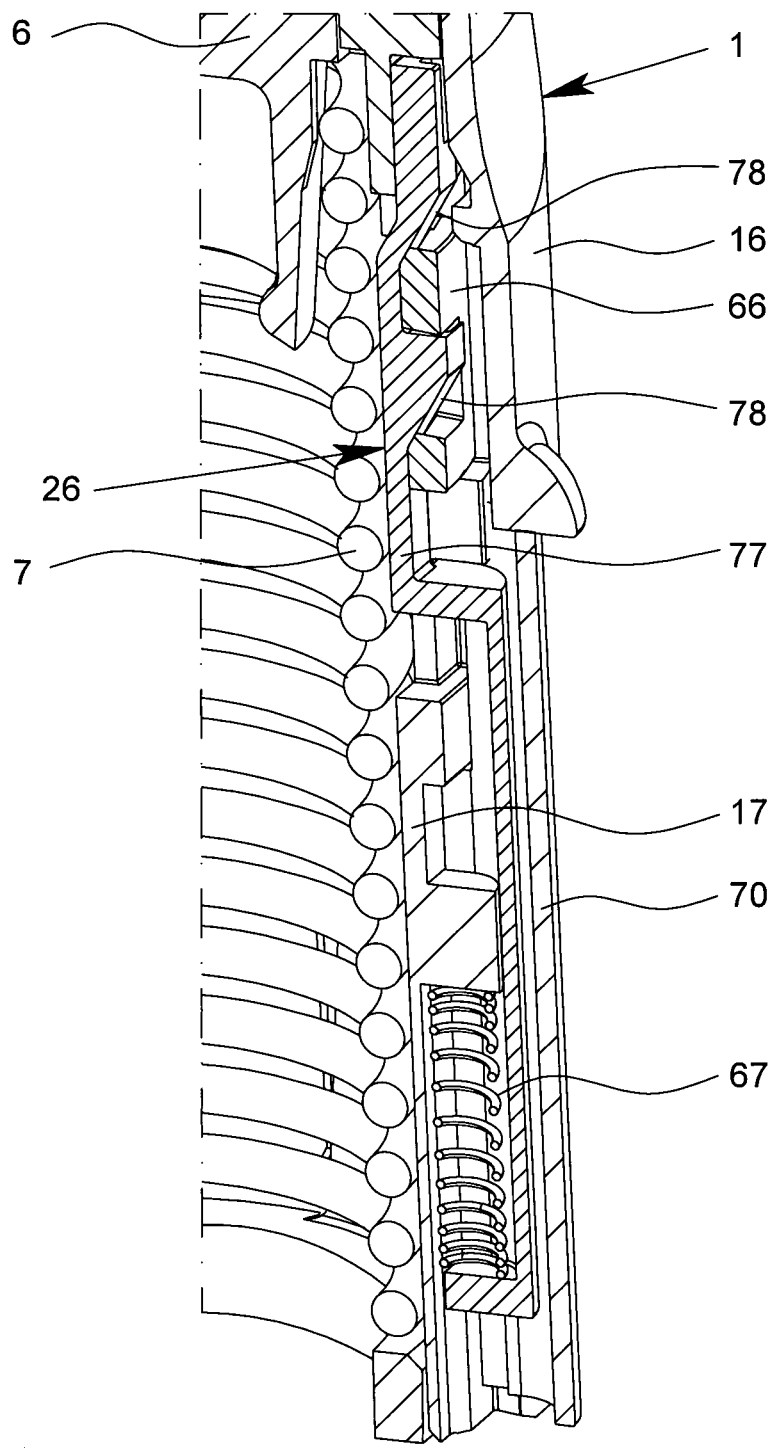
FIG. 24 a perspective section of the nebulizer with the unlocked locking device according to a further embodiment.
Figure 25:
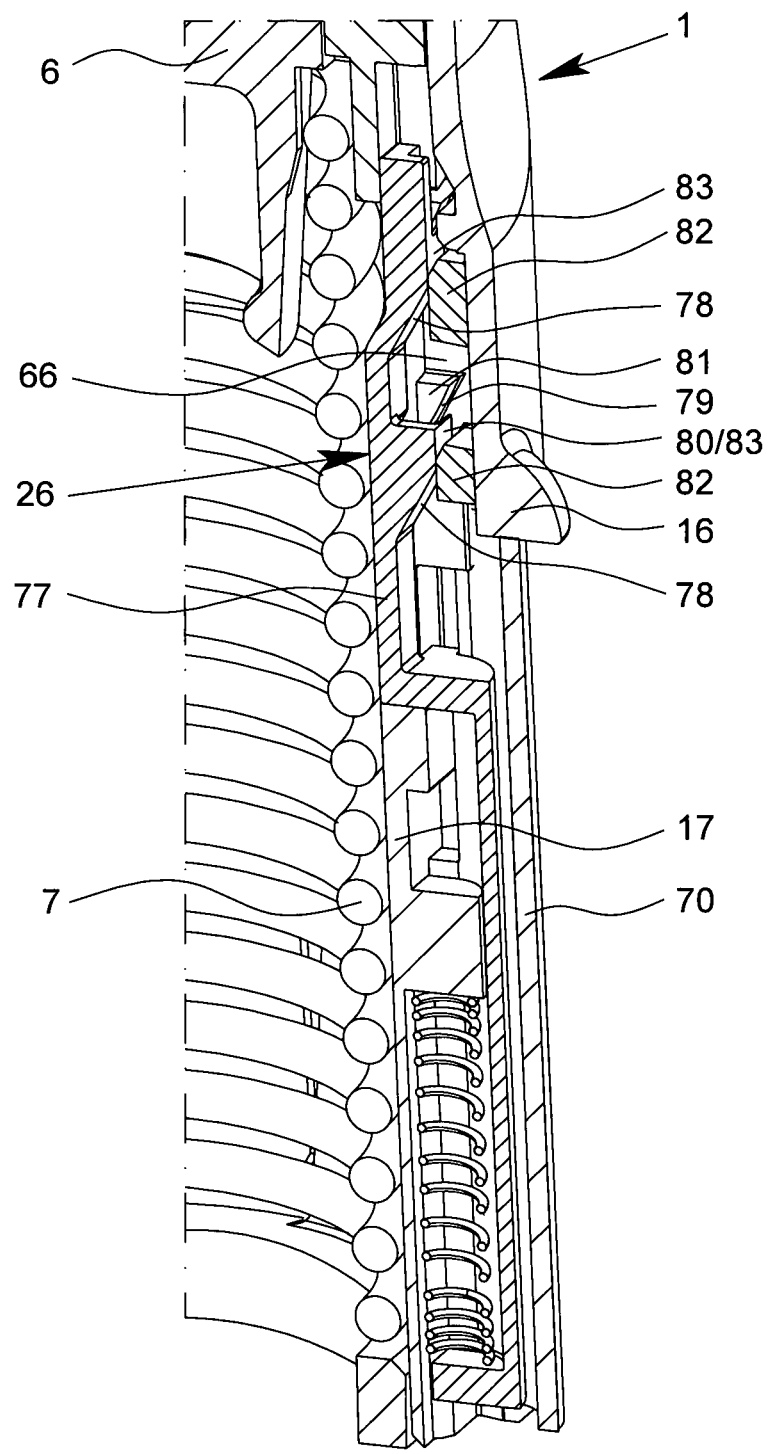
FIG. 25 a schematic section similar to FIG. 24 with the locking device in the locking position.

In the present embodiment, the locking element 66 is (only) axially moveable between the locking and non-locking position and vice versa. However, the locking element 66 can be moveable alternatively or additionally in radial direction to switch between the locking and non-locking position or vice versa, as explained later with regard to FIGS. 24 and 25 showing a further embodiment. For example, the locking element 66 may be pushed radially outwards, in particular to engage in a respective groove or recess or the like in the locking position, in order to block (further) tensioning or use of the nebulizer 1.

In particular, the locking element 66 may form or may be formed by a sliding block.

In the present embodiment, the locking spring 67 is preferably arranged at the lower part 17b of the inner part 17 and/or at the lower end of the locking device 26 or locking element 66, or near or adjacent to the housing part 18. However, the locking spring 67 can also be arranged at the other end and/or within the upper housing part 16 of the nebulizer 1 as shown in FIG. 23 and/or at any other convenient location.

Figure 23:
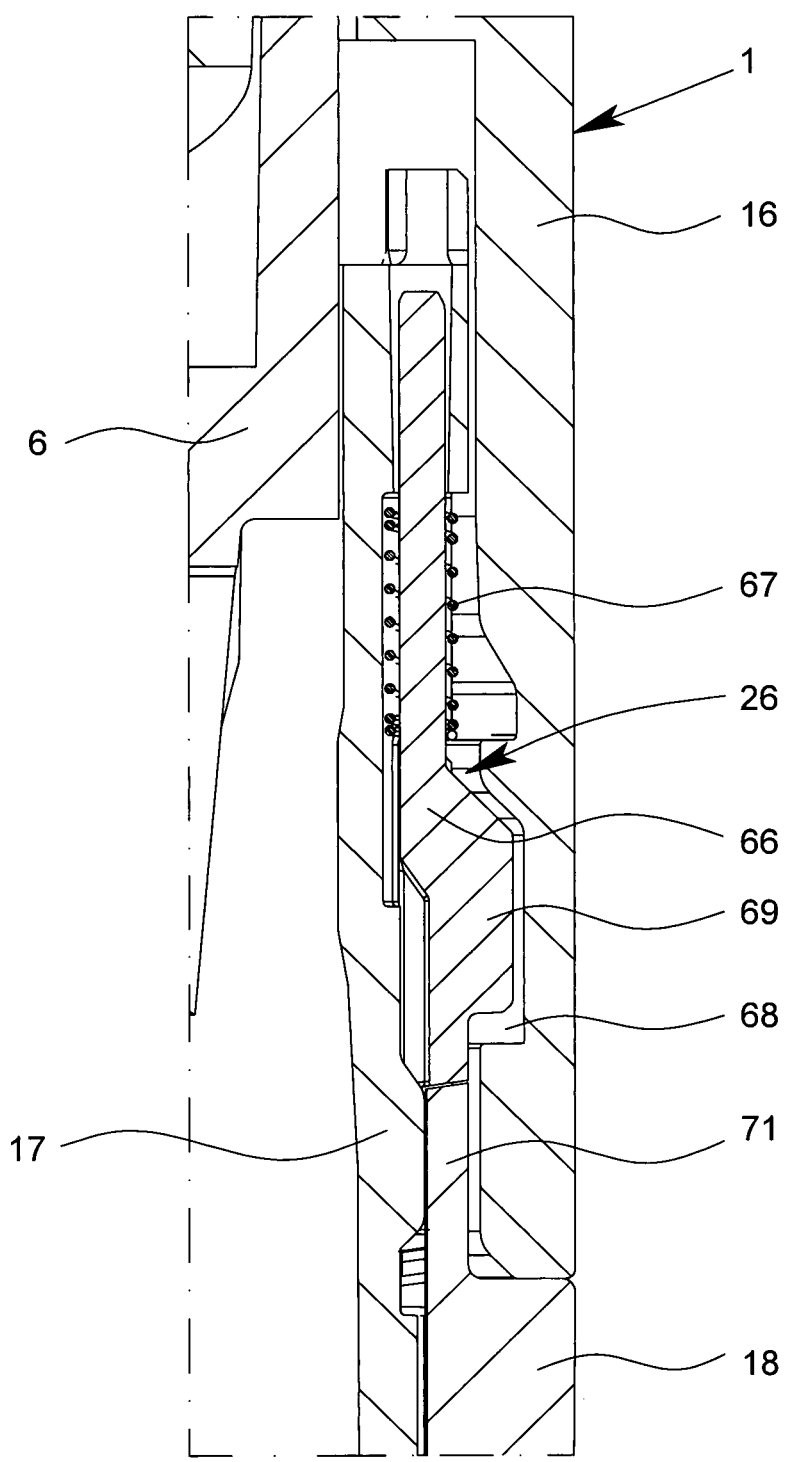
FIG. 23 a partial schematic section of the nebulizer with unlocked locking device according to another embodiment.

FIG. 23 shows in a partial schematic section the locking device 26 according to another embodiment with differently arranged locking spring 67, namely in the upper housing part 16.

It has to be noted that the previous explanations apply also for the other embodiments and all further embodiments described in a similar or a corresponding manner, even if a respective repetition is omitted.

In the present embodiments, the locking spring 67 is preferably a push-spring or compression-spring. However, a pull-spring could be used alternatively.

In the present embodiments, the locking spring 66 is preferably a helical spring. However, it could be used alternatively e.g. a flat spring or leaf spring or any other spring.

In the present embodiments, the locking element 66 and the locking spring 67 are formed by separate parts. However, it is generally also possible to integrate the locking element 66 into the locking spring 67 or vice versa.

Figure 19:
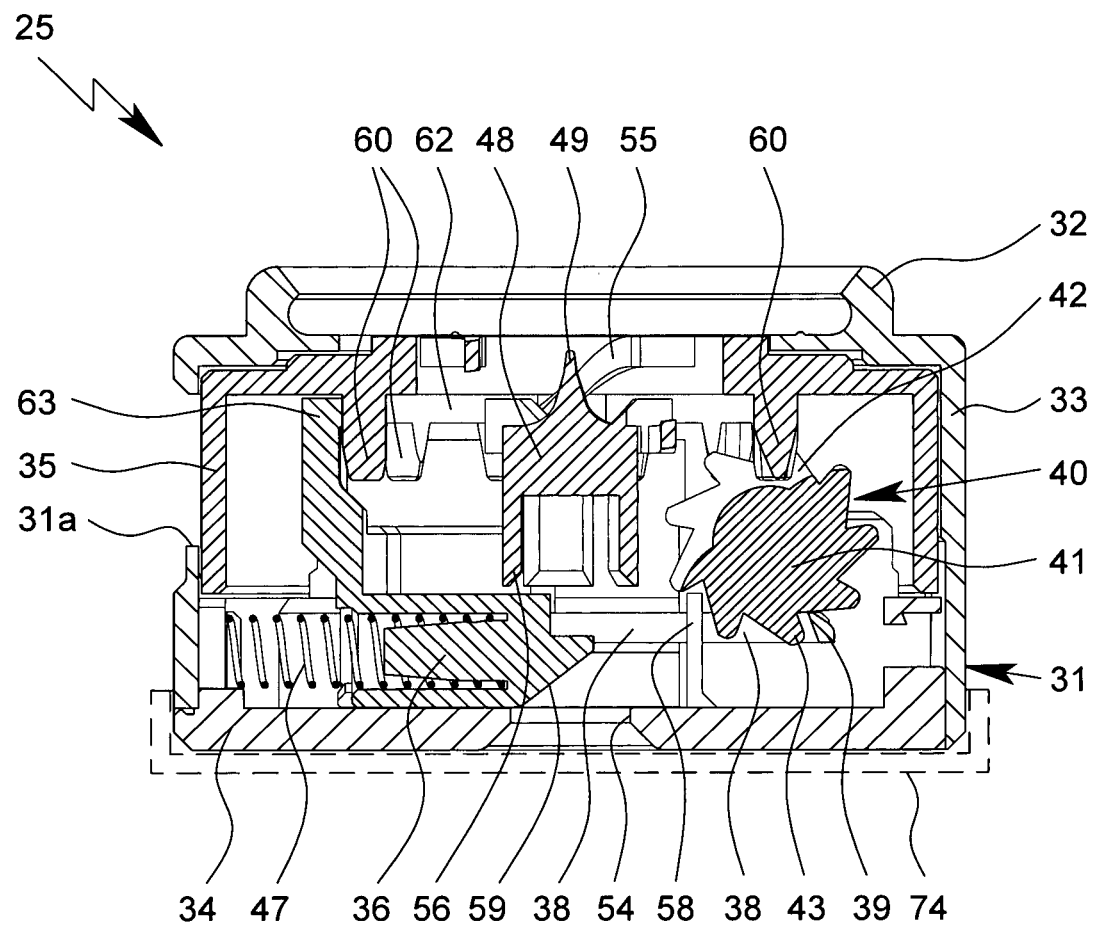
FIG. 19 a schematic section of the indicator device in the initial state according to a modified embodiment.

FIG. 19 shows in a schematic section the indicator device 25 according to a modified embodiment of the present invention. FIG. 20 shows a perspective view of the section according to FIG. 19.

In the following, only relevant differences are described so that the previous explanations and aspects apply in addition, in particular in the same or similar manner, without repetition.

In the modified embodiment, the actuation arm 38 and actuation portion 39 do not engage in between the worm drive, i.e. between the gear 41 and the engaging protrusions 60 of the driven part, here namely the indicator element 35, but engage with or actuate the gear 41 on another side or the side opposite the worm drive, here preferably in FIG. 19 from below and not from above. In particular, the actuation arm 38 extends more or less in a radial plane and/or more or less in a common plane with the actuation spring 47 and/or blocking part 61 or the sliding carriage part of the actuation element 36.

Preferably, the actuation arm 38 or portion 39 engages with the gear 41 on the side opposite the container 3 or gripping section 32.

In the modified embodiment, the indicator device 25 counts preferably when the nebulizer 1 is tensioned, i.e. during the tensioning process and not during the dispensing process as provided in the initial embodiment of the present invention.

In particular, the actuation element 36 or its arm 38 drives or rotates the transmission 40 or gear 41, when the driving part 52 is inserted into the indicator device 25, its housing 31 or its insertion opening 54 and/or when the actuation element 36 is moved from the first position to the second position and/or when the actuation element 36 is pushed transversally by the driving part 52. In the opposite direction, the actuation arm or its actuation portion 39 passes the next tooth 43 of the gear 41, i.e. does not drive the gear 41.

In the modified embodiment, the indicator device 25 or counting is not driven by the force of the actuation spring 47 or any other spring or energy store, but by the relative movement of the indicator device 25 within the nebulizer 1 or by the insertion of an actuator element, such as the driving part 52. However, other constructional solutions are possible as well.

In the modified embodiment, the blocking of the carriage/actuation element 36/locking part 61 to move into the third or locking position are released during the tensioning when a predetermined number of uses is reached or exceeded. Then, the carriage/actuation element 36/blocking part 61 abut against the driving part 52 because the counting occurs during the tensioning. When the nebulizer 1 is actuated or when the blocking element 8 is depressed, the nebulizer 1 is triggered and the (last) dose of fluid 2 is nebulized. During this nebulization, the driving part 52 is removed from the indicator device 25 or insertion opening 54 so that the carriage/actuation element 36/blocking part 61 are free to move into the third or locking position due to the force of the actuation spring 47 or any other spring means.

During the next tensioning, the nebulizer 1 or its housing 24 or housing part 18 will be partially opened when the driving part 52 abuts against the closed indicator device 25, in particular against the carriage/actuation element 36/blocking part 61 restricting or closing the insertion opening 54.

In the previous embodiment, the counting or actuating of the indicator device 25 takes place or occurs when dispensing fluid, i.e. when the driving part 52 is withdrawn from the insertion opening 54. There, the carriage/actuation element 36/blocking part 61 are released during the last use of the nebulizer 1 or dispensing, i.e. when moving from the second to the first position so that the carriage/actuation element 36/blocking part 61 can move further directly into the third or unlocking position. Thus, any later dispensing is not possible.

In both cases, i.e. in the previous embodiment and in the modified embodiment, the indicator device 25 blocks full axial or stroke-moveability of the container 3 within the nebulizer 1 in the locked state and/or causes at least partially opening of the nebulizer housing 24 and/or housing part 18 in the locked state, in particular when the nebulizer 1 is tensioned at least partially for the last time with the current container 3.

Further, the at least partial opening of the nebulizer 1 or its housing 24 or housing part 18 results in that the nebulizer 1 is blocked, in particular cannot be tensioned any further or used any further, with the current container 3.

Figure 20:
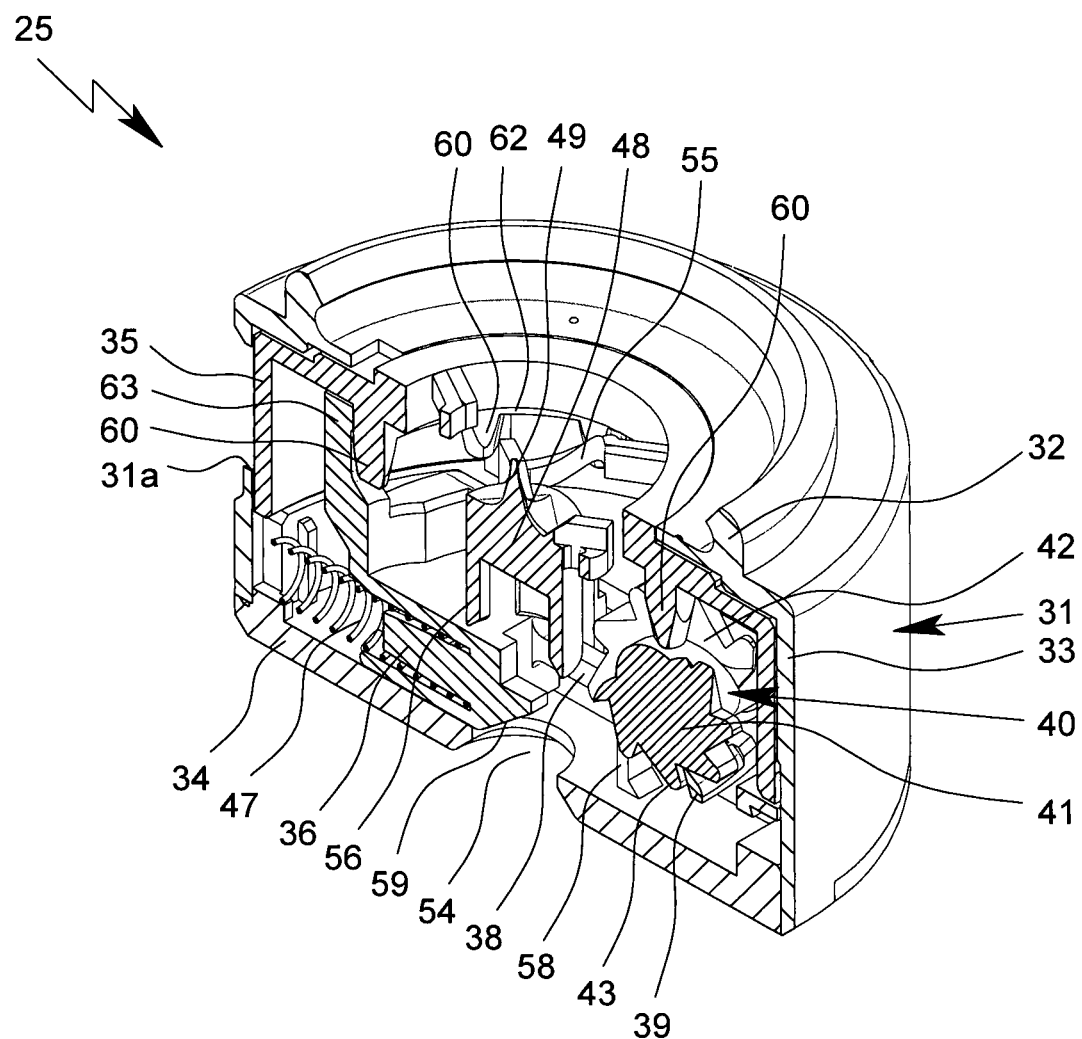
FIG. 20 a perspective section of the indicator device according to FIG. 19.

FIGS. 19 and 20 show the indicator device 26 according to the present invention in the non-actuated or initial state and/or with the actuation element 36 in the first position. The control part 63, which extends preferably upwards and/or in the axial direction, abuts against the preferably ring-like control portion 62 which is preferably formed by or at the indicator element 35. Preferably, the control portion 62 has a radial distance to the outer wall of the indicator element 35 so that the control part 63 can move inbetween and that the actuation element 36 is free to move between the first and second positions, while the abutment of the control part 63 against the control portion 62 prevents movement of the actuation element 36 from the first position further towards the third position and/or further to (complete) closing the insertion opening 54.

Preferably, the protrusions 60 are dent-like and/or are tapered towards its free ends.

Preferably, the protrusions 60 are formed on or connected with the control portion 62.

Generally, the insertion opening 54 is provided preferably with a conical surface or edge to facilitate insertion of the driving part 52 or the like.

Preferably, the support structure 55 forms or comprises one or more flexible arms for moveably holding the piercing part 48, preferably in the center of the indicator device 25 or its housing 31 or a respective opening of the housing 31, so that the piercing part 48 is usually held inside the indicator device 25 but can move and in particular protrude outwards and/or towards the container 3 for opening or piercing aeration. However, other constructional solutions are possible.

Generally, the indicator device 25 and the container 3 form an inseparable assembly or unit, which has to be replaced completely after use, in particular after reaching the locked state. However, it is also possible that the container 3 and indicator device 25 are supplied or offered as a kit which can be assembled by the use or patient.

Generally, the indicator device 25 cannot be reset after reaching the locked state so that it cannot be reused. However, it is also possible to modify the indicator device 25 such that it can be reset and reused. In this case, the indicator device 25 has to be separated from the present container 3 and connected with a new (unused) container 3. Most preferably, such a container change would automatically reset the indicator device 25.

It has to be noted that the insertion opening 54, which is preferably arranged centrally and/or opens in the axial direction and/or allows axial insertion of an actuator element, in particular the driving part 52 in the present embodiment, can also be formed as a recess, groove, indention or the like and/or can be arranged at any position or location at the indicator device 25 with any orientation.

Alternatively, the insertion opening 54 or its closing can also be omitted. Instead, the indicator device 25, actuation element 36 or blocking part 61 can more or less directly communicate with or actuate the locking device 26 or, for example, the retaining element 19 or blocking element 8 in order to cause a direct or indirect locking of the nebulizer 1 or container 3 against further use.

Generally, the actuation element 36 or blocking part 61 is moveable preferably linearly, in particular like a sliding carriage. In particular, a sliding carriage is formed.

Preferably, the sliding carriage forms a base part of the actuation element 36 or blocking part 61.

Preferably, the sliding carriage, actuation element 36 or blocking part 61 is moveably held by sliding guides 72 on opposite sides, preferably on opposite sides of the insertion opening 54, as schematically shown in FIGS. 8 and 9. Preferably, the guides 72 are formed by respective rails or the like of the housing 31 or its lower part 34 which grip over respective edges or base portions 73 of the actuation element 36 or blocking part 61 to form the desired sliding guidance. However, other constructional solutions are possible as well.

Instead of the preferably linear or sled-like moveable actuation element 36 and/or blocking part 61, any other motion, in particular a radial and/or pivotal movement, is possible, in particular for partially or completely closing the insertion opening 54.

Alternatively, the actuation element 36 and/or blocking part 61 can move outwards from the indicator device 25 or its housing 31, preferably transversally and/or at one side of the indicator housing 31 for locking at least one engagement possibility and/or actuating any other component in the locked state or for locking the nebulizer 1 and/or container 3.

Alternatively or additionally, the actuation element 36 and/or blocking part 61 can engage into or abut against a section or contour of the housing part 18 and/or nebulizer housing 24 or the like in order to restrict or prevent operation or movement in the locked state in order to block further use of the nebulizer 1 and/or container 3 in the locked state.

The actuation element 36 and/or blocking part 61, in particular also when acting radially, are preferably biased by spring 47 or any other spring means. The spring or spring means can be formed integrally and/or by plastic parts or pieces. Alternatively, a spiral or clock spring or any other spring, such as helical spring 47 or the like, could be used for biasing the actuation element 36 and/or blocking part 61, preferably into the locked state.

It is also possible that the driving part 52 directly drives or actuates the gear 41. In this case, the driving part 52 is preferably elastically supported by the housing part 18, in particular via a spring means (not shown), in particular for compensating axial tolerances and/or allowing radial or transversal flexing of the driving part 52. Additionally or alternatively, the driving part 52 may be flexible in order to allow transversal flexing for engaging with the gear 41 only in one direction of relative axial movement to the gear 41 to rotate the gear 41 only in one rotational direction.

The indicator device 25 can comprise any other counting mechanism, in particular as described in WO 2009/037085 A1, page 4, line 19 to page 10, line 13, which is incorporated herein by reference.

Such a counting mechanism can also trigger, release or actuate the actuation element 36 and/or blocking part 61. When using this counting mechanism, the rotatable indicator element 35 can also release or control the release of the carriage, actuation element 36 or blocking part 61 in the locked state to move into the third or locking position or close the insertion opening 54.

It is also possible that the carriage or blocking part 61 is independent from the counting. In particular, the driving part 52 may engage the hub of the counting mechanism shown in WO 2009/037085 A1 or the like and/or drive or actuate the indicator device 25 or counting without actuating the carriage or blocking part 61. In this case, the functions are separated. The carriage and/or blocking part 61 are preferably used only for restricting or closing the insertion opening 54 in the locked state, but not for actuating or driving the indicator device 25 of its counting mechanism or transmission 40 or indicator element 35 or the like.

The container 3 or indicator device 25 or insertion opening 54 may be provided with an optional protection 74, shown schematically only in FIG. 19, which covers in particular the insertion opening 54 before the first use.

Preferably, the protection 74 has to be removed before the container 3 and/or indicator device 25 can be inserted into the nebulizer 1 or housing part 18.

Preferably, the protection 74 extends transversally over the indicator device 25 or its housing 31 and/or over the container 3 and/or has a larger diameter than the indicator device 25 and/or container 3, in particular such that it does not fit into the nebulizer 1 or housing part 18.

Preferably, the protection 74 can be removed only irreversibly, i.e. cannot be re-connected after removal.

Preferably, the protection 74 covers or closes the insertion opening 54 and/or the indicator device 25.

Preferably, the protection 74 is connected to the indicator device 25 or container 3 by form-fit or force-fit and/or by a snap-fit or click-fit.

In the following, a further embodiment of the nebulizer 1 and, in particular, of the locking device 26 will be described with reference to FIGS. 24 and 25. The following description will focus on relevant differences and new aspects in particular in comparison to the embodiment according to FIGS. 16 to 18, 21 and 22, wherein the previous explanations and features shall preferably apply respectively or in a corresponding manner for the further and other embodiment even if a respective description is omitted.

FIG. 24 shows in a partial schematic section of the nebulizer 1, the locking device 26 of the further embodiment in the unlocked position. FIG. 25 shows the locking device 26 in a respective section, but in the locked position or state.

In the further embodiment, the locking element 66 is preferably formed as a sliding block which is preferably moveable (only) radially.

In the further embodiment, the locking device 26 comprises preferably a locking member 77 interacting with the locking element 66 via at least one inclined surface 78 for actuating, in particular radially moving the locking element 66 into the locking position.

Preferably, the locking element 66 is moved into the locking position by form-fit engagement or actuation, here of the locking member 77 or inclined surface 78.

The locking element 66 is preferably moveable positively from the unlocked position into the locked position and/or vice versa.

The locking element 66 is preferably moveable back into the unlocked position by form-fit engagement and/or by reverse or upward movement of the locking member 77 and/or engagement or abutment of a respective, preferably inclined control surface 79 of the locking element 66 as schematically shown in FIG. 25.

In the further embodiment, the control surface 79 cooperates with a respective wall or angled portion 80 of the locking member 77 as schematically shown in FIG. 25 in order to transform the preferably linear and/or axial movement of the locking member 77 into the lateral or radial—here unlocking or inwards—movement of the locking element 66 into the unlocked position.

Preferably, the control surface 79 is formed at or by a control portion 81 of the locking element 66. However, other constructional solutions are possible. For example, the inclined control surface 79 can additionally or alternatively be formed or built at or by the angled portion 80 or locking member 77 in order to realize the positive movement, here radially inwards, opposite to the locking movement, here radially outwards.

Generally, the locking element 66 is preferably reversible from the locking position into the unlocking position for releasing the rotational blocking or locked state. This is realized in the present embodiment preferably by axial actuation or upward movement of the locking member 77 by the axially abutting actuator 71 when closing the nebulizer 1 or its housing part 18. However, other constructional solutions are possible as well.

The above principle of transforming the axial movement or actuation into a radial movement applies also preferably in the opposite direction, i.e. when actuating or locking the locking element 66.

In the further embodiment, the inclined surface 78 cooperates preferably with a counter portion 82 formed at or by the locking element 66.

It is also possible to form the inclined surface 78 and/or a corresponding counter surface at or by the counter portion 82 or locking element 66 in order to transform the linear or axial movement of the locking member 77 into the desired lateral or radial locking movement, here radially outwards.

In the further embodiment, the locking member 77 comprises preferably two inclined surfaces 78 and the locking element 66 comprises preferably two counter portions 82 in order to precisely move or actuate the locking element 66 and/or to move the locking element 66 without any or minimized tilting. Thus, the linear or axial movement or actuation of the locking member 77 can be transformed into a lateral or transversal or radial or outwards movement of the locking element 66 into the locked position shown in FIG. 25.

Preferably, the locking element 66 is held or locked in the locked position by an at least essentially flat or axial bearing portion or surface 83, in particular two surfaces 83.

Preferably, the locking member 77 forms the essentially flat or axial bearing surface(s) 83 to hold or lock the locking element 66 in the locked position.

In particular, the counter portion(s) 82 can move along the respective inclined surface 78 during the axial—here downward—movement of the locking member 77 and, then, reach the respective bearing surface 83. This state is shown in FIG. 25.

Generally, the locking element 66 can consist of or the locking device 26 can comprise at least one or more locking elements 66—preferably with one or multiple engagement portions 69—distributed around or on the circumference of the inner part 17 and/or biased preferably in parallel and/or in the axial direction into a locking position by one or more locking springs 67. This modification is not shown, but would allow very secure blocking in the locked state.

As already mentioned, individual features, aspects and/or principles of the embodiments described may also be combined with one another as desired and may be used particularly in the shown nebulizers 1 but also in similar or different nebulizers.

Features of the different embodiments can be combined or exchanged.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers, e.g. powder inhalers or so-called metered dose inhalers.

Preferably, the fluid 2 is a liquid, as already mentioned, especially an aqueous pharmaceutical formulation or an ethanolic pharmaceutical formulation. However, it may also be some other pharmaceutical formulation, a suspension or the like.

According to an alternative embodiment the fluid 2 may also comprise particles or powder. In this case, instead of the expulsion nozzle 12, some other kind of supply device may be provided, especially an expulsion opening (not shown) or a supply channel (not shown) for supplying the fluid to or powder or the like into the mouthpiece 13. The optional air supply opening 15 then serves to supply ambient air preferably in parallel so as to general or allow an airflow with a sufficient volume for breathing in or inhaling through the mouthpiece 13.

If necessary the fluid 2 may also be atomized by means of a propellant gas.

Preferred ingredients and/or formulations of the preferably medicinal fluid 2 are listed in particular in WO 2009/115200 A1, preferably on pages 25 to 40, or in EP 2 614 848 A1, paragraphs 0040 to 0087, which are incorporated herewith by reference. In particular, these may be aqueous or non-aqueous solutions, mixtures, formulations containing ethanol or free from any solvent, or the like.

LIST OF REFERENCE NUMERALS 1 nebulizer
2 fluid
3 container
4 bag
5 pressure generator
6 holder
7 drive spring
8 blocking element
9 conveying tube
10 non-return valve
11 pressure chamber
12 nozzle
13 mouthpiece
14 aerosol
15 air supply opening
16 upper housing part
17 inner part
17a upper part of inner part
17b lower part of inner part
18 housing part (lower part)
19 retaining element 50 foil
20 aeration spring
21 container base
22 piercing element
23 venting hole
24 nebulizer housing
25 indicator device
26 locking device
27 mouthpiece cover
28 head
29 container housing
30 container edge
31 indicator housing
31a window
32 gripping section
33 upper part
34 lower part
35 indicator element
36 actuation element
37 marking
38 actuation arm
39 actuation portion
40 transmission
41 gear
42 worm
43 tooth
44 axle section
45 bearing section
46 bearing portion
47 actuation spring
48 piercing part
49 piercing tip
51 indention
52 driving part
53 bottom
54 insertion opening
55 support structure
56 flexible arm
57 groove
58 ratchet
59 surface
60 protrusion
61 blocking part
62 control portion
63 control part
64 retaining nose
65 retaining recess
66 locking element
67 locking spring
68 pocket
69 engagement portion
70 cover
71 actuator
72 sliding guide
73 base portion
74 protection
75 groove
76 protrusion
77 locking member
78 inclined surface
79 control surface
80 angled portion
81 control portion
82 counter portion
83 bearing surface

The invention claimed is:

1. A nebulizer (1) for a fluid (2), the nebulizer (1) comprising:
an upper housing part (16);
a lower housing part (18);
a replaceable or insertable container (3) containing the fluid (2);
an indicator device (25) for counting or indicating a number of uses performed or still possible with the container (3); and
a locking device (26) adapted to block further use of the nebulizer (1) or container (3) in a locked state when a predetermined number of uses has been reached or exceeded with the current container (3), wherein:
the nebulizer (1) is tensioned for next use by a rotation of the lower housing part (18) relative to the upper housing part (16), such rotation about a predetermined total rotation angle being necessary for reaching a complete tensioned state for the next use of the nebulizer (1), and
the locking device (26), or a locking element (66) thereof, is adapted to block the rotation of the lower housing part (18) at an intermediate position after initiating the rotation of the lower housing part (18), but before reaching the predetermined total rotation angle, and thereby before reaching the complete tensioned state of the nebulizer (1).

2. The nebulizer (1) for a fluid (2), according to claim 1, wherein at least one of:
the locking element (66) axially engages, by form-fit, in a locking position to block the rotation, and
that the locking element (66) engages with multiple engagement portions (69) into respective pockets (68) or vice versa in a locking position to block the rotation.

3. The nebulizer according to claim 1, wherein the locking device (26) comprises the locking element (66), which is movable via an associated locking spring (67).

4. The nebulizer according to claim 3, wherein the locking element (66) is biased into a locking position by the locking spring (67).

5. The nebulizer according to claim 3, wherein the locking spring (67) biases the locking element (66) into the locking position, so that upon at least partial opening of the nebulizer (1) or axial displacement of the housing part (18), the locking device (26), or the locking element (66), moves into the locking position.

6. The nebulizer according to claim 3, wherein the locking element (66) comprises at least one or more such locking elements (66), each having one or multiple engagement portions (69) distributed on a circumferences of an inner part (17), which are biased in parallel into the locking position by the locking spring (67), or a plurality of such locking springs (67).

7. The nebulizer according to claim 3, wherein the locking spring (67) is a helical spring.

8. The nebulizer according to claim 5, wherein the locking element (66), moves into the locking position during a next rotation.

9. The nebulizer according to claim 3, wherein the locking spring (67) is a compression spring.

10. The nebulizer according to claim 1, wherein the locking element (66) is moveable only radially.

11. The nebulizer according to claim 1, wherein the locking element (66) is moveable essentially or only in an axial direction.

12. The nebulizer according to claim 1, wherein the locking element (66) is formed by one single or rigid part.

13. The nebulizer according to claim 1, wherein the locking device (26) comprises an axially moveable locking member (77) interacting with the locking element (66) via at least one inclined surface (78) for radially moving the locking element (66) into the locking position or vice versa.

14. The nebulizer according to claim 1, wherein the locking device (26) comprises a sliding block as the locking element (66).

15. The nebulizer according to claim 1, wherein the locking element (66) is reversible from the locking position into an unlocking position for releasing the rotational blocking or locked state.

16. The nebulizer (1) for a fluid (2), according to claim 1, wherein the locking device (26) can be reset to release the rotational locking.

17. The nebulizer according to claim 1, wherein, after replacement of the container (3) having a locked indicator device (25) with a new container (3) including a reset indicator device (25), the nebulizer (1) is closed completely so that the nebulizer (1) and its locking device (26) is automatically unlocked.

18. The nebulizer according to claim 1, wherein the housing part (18) comprises a finger-like or axially extending actuator (71) which extends into the locking device (26) or into a cover (70), or axially abuts and/or pushes the locking element (66) into its unlocking position, such that only the completely closed nebulizer (1) unlocks the locking device (26) and, thus, unlocks the nebulizer (1).

19. The nebulizer according to claim 1, wherein the actuator (71) is arranged within the housing part (18).

20. The nebulizer according to claim 1, wherein the locking spring (67) is arranged at a lower part (17*b*) of the inner part (17) or at the lower end of the locking device (26) or locking element (66), or near or adjacent to the housing part (18).

21. The nebulizer according to claim 3, wherein the locking spring (67) is arranged within the upper housing part (16) of the nebulizer (1).

22. The nebulizer according to claim 3, wherein the locking element (66) and the locking spring (67) are formed by separate parts.

23. The nebulizer according to claim 1, wherein, in the locking position, the locking device (26) or the locking element (66) blocks rotation of an inner part (17) of the nebulizer (1) relative to the upper part (16) of the nebulizer (1) and, thus, blocks further rotation and tensioning of the nebulizer (1).

24. The nebulizer according to claim 1, wherein the indicator device (25) is moveable axially with the container (3) within the nebulizer (1), during supplying or nebulizing the fluid (2) or tensioning the nebulizer (1).

25. The nebulizer according to claim 1, wherein the indicator device (25) is arranged at the container (3) and moveable together with the container (3) axially within the nebulizer (1) during rotation, nebulization or tensioning.

26. The nebulizer according to claim 1, wherein the locking device (26) or the locking element (66) is adapted to block actuation of the nebulizer (1), triggering the nebulization of a dose of the fluid (2), or the release of a spring (7) or holder (6) to dispense the fluid (2), by blocking any depression of a blocking element (8).

27. The nebulizer according to claim 1, wherein the container (3) is replaceable in an at least partially tensioned state of the nebulizer (1), such that complete closing of the nebulizer (1) or its housing (24) is not possible when the indicator device (25) is in the locked state.

28. The nebulizer according to claim 1, wherein the locking device (26) is controlled or controllable by the indicator device (25).

29. The nebulizer according to claim 16,
wherein the locking element (66) of the locking device (26) is adapted to block the rotation when the predetermined number of uses has been reached or exceeded with the container (3) via movement of the locking element (66) from a first position, in which the rotation is not blocked in an unlocked state, to a second position, in which the rotation is blocked in the locked state, and
the locking device (26) is resettable, where the locking element (66) is moved from the second position back to the first position in which the rotation is not blocked in an unlocked state.

30. The nebulizer according to claim 29, wherein:
the locking element (66) moves one of axially and radially from the first position to the second position to block the rotation in the locked state, and
the locking element (66) moves the one of axially and radially from the second position to the first position to unblock the rotation in the unlocked state.

31. The nebulizer according to claim 1, wherein the intermediate position is in a second half of the predetermined total rotation angle.

\* \* \* \* \*